(12) United States Patent
Nakajima et al.

(10) Patent No.: US 11,617,516 B2
(45) Date of Patent: Apr. 4, 2023

(54) BIOLOGICAL INFORMATION ANALYSIS DEVICE, BIOLOGICAL INFORMATION ANALYSIS SYSTEM, PROGRAM, AND BIOLOGICAL INFORMATION ANALYSIS METHOD

(71) Applicants: OMRON Corporation, Kyoto (JP); OMRON HEALTHCARE Co., Ltd., Kyoto (JP)

(72) Inventors: Hiroshi Nakajima, Kyoto (JP); Hirotaka Wada, Kyoto (JP); Naoki Tsuchiya, Otsu (JP); Masaaki Kasai, Nara (JP); Eriko Kan, Kyoto (JP); Toru Uenoyama, Kyoto (JP); Keiichi Obayashi, Tokyo (JP); Ayako Kokubo, Uji (JP); Yuya Ota, Kyoto (JP); Toshikazu Shiga, Otsu (JP); Mitsuo Kuwabara, Hirakata (JP); Hironori Sato, Moriyama (JP); Ken Miyagawa, Kyoto (JP); Masakazu Tsutsumi, Muko (JP)

(73) Assignees: Omron Corporation, Kyoto (JP); OMRON HEALTHCARE Co., Ltd., Kyoto (JP)

( * ) Notice: Subject to any disclaimer, the term of this patent is extended or adjusted under 35 U.S.C. 154(b) by 533 days.

(21) Appl. No.: 16/092,097

(22) PCT Filed: Apr. 14, 2017

(86) PCT No.: PCT/JP2017/015274
§ 371 (c)(1),
(2) Date: Oct. 8, 2018

(87) PCT Pub. No.: WO2017/179693
PCT Pub. Date: Oct. 19, 2017

(65) Prior Publication Data
US 2019/0117095 A1  Apr. 25, 2019

(30) Foreign Application Priority Data

Apr. 15, 2016 (JP) .............................. JP2016-082463

(51) Int. Cl.
*A61B 5/024* (2006.01)
*A61B 5/022* (2006.01)
(Continued)

(52) U.S. Cl.
CPC ............ *A61B 5/029* (2013.01); *A61B 5/0002* (2013.01); *A61B 5/021* (2013.01); *A61B 5/022* (2013.01);
(Continued)

(58) Field of Classification Search
CPC .... G16H 10/40; G16H 50/20; A61B 5/02108; A61B 5/681
See application file for complete search history.

(56) References Cited

U.S. PATENT DOCUMENTS 4,365,636 A   12/1982  Barker
5,400,793 A    3/1995  Wesseling
(Continued)

FOREIGN PATENT DOCUMENTS

CN   1140582 A   1/1997
CN   1158077 A   8/1997
(Continued)

OTHER PUBLICATIONS

Appendix 1 to the Oct. 2019 Update: Subject Matter Eligibility, Life Sciences & Data Processing Examples (Year: 2019).*
(Continued)

*Primary Examiner* — Christian Jang
(74) *Attorney, Agent, or Firm* — Osha Bergman Watanabe & Burton LLP

(57) ABSTRACT

A biological information analyzing device includes: an indicator extraction unit that extracts an indicator pertaining
(Continued)

to a characteristic of a blood pressure waveform using data of the blood pressure waveform obtained by a sensor, which is worn on a user's body and can non-invasively measure the blood pressure waveform for each of heartbeats, continuously measuring the blood pressure waveform; and a processing unit that carries out a process based on the extracted indicator.

8 Claims, 8 Drawing Sheets

(51) Int. Cl.
| | |
|---|---|
| A61B 5/0205 | (2006.01) |
| G16H 10/40 | (2018.01) |
| G16H 50/20 | (2018.01) |
| A61B 5/02 | (2006.01) |
| A61B 5/029 | (2006.01) |
| A61B 5/08 | (2006.01) |
| A61B 5/316 | (2021.01) |
| A61B 5/352 | (2021.01) |
| A61B 5/021 | (2006.01) |
| A61B 5/00 | (2006.01) |
| A61B 5/11 | (2006.01) |
| A61M 16/00 | (2006.01) |
| A61F 5/56 | (2006.01) |
| A61M 21/00 | (2006.01) |
| G06F 1/16 | (2006.01) |
| A61B 5/145 | (2006.01) |
| A61B 5/026 | (2006.01) |

(52) U.S. Cl.
CPC ............ *A61B 5/024* (2013.01); *A61B 5/0205* (2013.01); *A61B 5/02028* (2013.01); *A61B 5/02055* (2013.01); *A61B 5/02108* (2013.01); *A61B 5/02116* (2013.01); *A61B 5/02125* (2013.01); *A61B 5/02225* (2013.01); *A61B 5/02233* (2013.01); *A61B 5/02438* (2013.01); *A61B 5/08* (2013.01); *A61B 5/0816* (2013.01); *A61B 5/1118* (2013.01); *A61B 5/316* (2021.01); *A61B 5/352* (2021.01); *A61B 5/4818* (2013.01); *A61B 5/4836* (2013.01); *A61B 5/4884* (2013.01); *A61B 5/681* (2013.01); *A61B 5/6801* (2013.01); *A61B 5/6824* (2013.01); *A61B 5/721* (2013.01); *A61B 5/7221* (2013.01); *A61B 5/7239* (2013.01); *A61B 5/7275* (2013.01); *A61B 5/7278* (2013.01); *A61B 5/7282* (2013.01); *A61B 5/742* (2013.01); *A61B 5/743* (2013.01); *A61B 5/746* (2013.01); *A61F 5/56* (2013.01); *A61M 16/024* (2017.08); *A61M 21/00* (2013.01); *G06F 1/163* (2013.01); *G16H 10/40* (2018.01); *G16H 50/20* (2018.01); *A61B 5/026* (2013.01); *A61B 5/02141* (2013.01); *A61B 5/14532* (2013.01); *A61B 5/14542* (2013.01); *A61B 5/4806* (2013.01); *A61B 5/683* (2013.01); *A61B 5/7203* (2013.01); *A61B 5/7257* (2013.01); *A61B 2560/0242* (2013.01); *A61B 2562/029* (2013.01); *A61M 2021/0022* (2013.01); *A61M 2021/0027* (2013.01); *A61M 2021/0044* (2013.01); *A61M 2021/0083* (2013.01)

(56) References Cited

U.S. PATENT DOCUMENTS

| | | | |
|---|---|---|---|
| 5,749,366 | A | 5/1998 | Odagiri et al. |
| 5,772,601 | A | 6/1998 | Oka et al. |
| 5,836,884 | A | 11/1998 | Chio |
| 5,857,975 | A | 1/1999 | Golub |
| 5,865,756 | A | 2/1999 | Peel, III |
| 5,941,837 | A | 8/1999 | Amano et al. |
| 5,980,464 | A | 11/1999 | Tsuda |
| 6,030,342 | A | 2/2000 | Amano et al. |
| 6,042,549 | A | 3/2000 | Amano et al. |
| 6,081,742 | A | 6/2000 | Amano et al. |
| 6,091,973 | A | 7/2000 | Colla et al. |
| 6,095,984 | A | 8/2000 | Amano et al. |
| 6,126,595 | A | 10/2000 | Amano et al. |
| 6,287,262 | B1 | 9/2001 | Amano et al. |
| 6,293,915 | B1 | 9/2001 | Amano et al. |
| 6,331,159 | B1 | 12/2001 | Amano et al. |
| 6,334,850 | B1 | 1/2002 | Amano et al. |
| 6,361,501 | B1 | 3/2002 | Amano et al. |
| 6,443,906 | B1 | 9/2002 | Ting et al. |
| 6,554,763 | B1 | 4/2003 | Amano et al. |
| 6,955,648 | B2 | 10/2005 | Mozayeni et al. |
| 2002/0173726 | A1 | 11/2002 | Narimatsu |
| 2003/0000522 | A1 | 1/2003 | Lynn et al. |
| 2003/0004421 | A1 | 1/2003 | Ting et al. |
| 2003/0004423 | A1 | 1/2003 | Lavie et al. |
| 2003/0088184 | A1 | 5/2003 | Kelly |
| 2003/0149369 | A1 | 8/2003 | Gallant et al. |
| 2003/0163034 | A1 | 8/2003 | Dekker |
| 2003/0204143 | A1 | 10/2003 | Lin |
| 2003/0204144 | A1 | 10/2003 | Lin |
| 2004/0044276 | A1 | 3/2004 | Arnold |
| 2004/0176692 | A1 | 9/2004 | Kario et al. |
| 2004/0210143 | A1 | 10/2004 | Gallant et al. |
| 2005/0075531 | A1 | 4/2005 | Loeb et al. |
| 2005/0096557 | A1 | 5/2005 | Vosburgh et al. |
| 2005/0187480 | A1 | 8/2005 | Kario et al. |
| 2006/0036126 | A1 | 2/2006 | Ross et al. |
| 2006/0047202 | A1 | 3/2006 | Elliott |
| 2006/0142663 | A1 | 6/2006 | Sawanoi et al. |
| 2006/0195035 | A1* | 8/2006 | Sun ................. A61B 5/022 600/503 |
| 2006/0200011 | A1 | 9/2006 | Suzuki et al. |
| 2007/0016095 | A1 | 1/2007 | Low et al. |
| 2007/0021673 | A1* | 1/2007 | Arbel ............... A61B 5/02116 600/500 |
| 2007/0118028 | A1 | 5/2007 | Kitajima et al. |
| 2007/0167843 | A1 | 7/2007 | Cho et al. |
| 2007/0282227 | A1 | 12/2007 | Nanba et al. |
| 2008/0027331 | A1 | 1/2008 | Suzuki et al. |
| 2008/0064965 | A1 | 3/2008 | Jay et al. |
| 2008/0200774 | A1 | 8/2008 | Luo |
| 2008/0262362 | A1 | 10/2008 | Kolluri et al. |
| 2008/0294021 | A1 | 11/2008 | Lin et al. |
| 2009/0124914 | A1 | 5/2009 | Kuo et al. |
| 2009/0216132 | A1 | 8/2009 | Orbach |
| 2009/0227425 | A1 | 9/2009 | Shirasaki et al. |
| 2010/0081947 | A1 | 4/2010 | Suzuki |
| 2010/0121207 | A1 | 5/2010 | Moersdorf et al. |
| 2010/0130874 | A1 | 5/2010 | Joeken |
| 2010/0222650 | A1 | 9/2010 | Tanishima et al. |
| 2010/0228139 | A1 | 9/2010 | Nanba et al. |
| 2010/0268097 | A1 | 10/2010 | Hatib et al. |
| 2010/0298721 | A1 | 11/2010 | Kim et al. |
| 2011/0015531 | A1 | 1/2011 | Fujii et al. |
| 2011/0077534 | A1 | 3/2011 | Kobayashi et al. |
| 2011/0077536 | A1 | 3/2011 | Kubo |
| 2011/0098540 | A1 | 4/2011 | Tanishima et al. |
| 2011/0152651 | A1 | 6/2011 | Berkow |
| 2011/0166458 | A1 | 7/2011 | Gallant et al. |
| 2011/0190643 | A1 | 8/2011 | Zhang et al. |
| 2011/0224748 | A1 | 9/2011 | Lippert et al. |
| 2011/0230729 | A1 | 9/2011 | Shirasaki et al. |
| 2012/0029361 | A1 | 2/2012 | Addison et al. |
| 2012/0108983 | A1 | 5/2012 | Banet et al. |
| 2012/0125337 | A1 | 5/2012 | Asanoi |

(56) References Cited

U.S. PATENT DOCUMENTS

| | | |
|---|---|---|
| 2013/0053664 A1 | 2/2013 | Jian et al. |
| 2013/0085079 A1 | 4/2013 | Gill et al. |
| 2013/0184545 A1 | 7/2013 | Blomqvist et al. |
| 2014/0018687 A1 | 1/2014 | Mano |
| 2014/0058220 A1 | 2/2014 | LeBoeuf et al. |
| 2014/0081101 A1 | 3/2014 | Shirasaki et al. |
| 2014/0163399 A1 | 6/2014 | Gallant et al. |
| 2014/0213858 A1 | 7/2014 | Presura et al. |
| 2014/0247970 A1 | 9/2014 | Taylor |
| 2014/0257124 A1 | 9/2014 | Morita |
| 2014/0275937 A1 | 9/2014 | Goedje et al. |
| 2014/0276071 A1 | 9/2014 | Hunziker et al. |
| 2014/0276123 A1 | 9/2014 | Yang |
| 2014/0303509 A1 | 10/2014 | Campbell |
| 2015/0038802 A1 | 2/2015 | Ezoe et al. |
| 2015/0099991 A1 | 4/2015 | Yamaguchi et al. |
| 2015/0109124 A1 | 4/2015 | He et al. |
| 2015/0164351 A1 | 6/2015 | He et al. |
| 2015/0168423 A1 | 6/2015 | Gill et al. |
| 2015/0196209 A1 | 7/2015 | Morris et al. |
| 2015/0245772 A1 | 9/2015 | Kawamoto et al. |
| 2015/0305632 A1 | 10/2015 | Najarian et al. |
| 2016/0058385 A1 | 3/2016 | Ajima |
| 2017/0209052 A1 | 7/2017 | Nakamura |
| 2017/0209074 A1 | 7/2017 | Siu et al. |
| 2017/0224227 A1 | 8/2017 | Kitagawa et al. |
| 2018/0028075 A1 | 2/2018 | Presura et al. |
| 2018/0078157 A1 | 3/2018 | Yang |
| 2018/0333056 A1 | 11/2018 | Chou |
| 2019/0083723 A1 | 3/2019 | Asanoi |
| 2020/0166523 A1 | 5/2020 | Gill et al. |

FOREIGN PATENT DOCUMENTS

| | | |
|---|---|---|
| CN | 1195277 A | 10/1998 |
| CN | 1199347 A | 11/1998 |
| CN | 1243425 A | 2/2000 |
| CN | 1430484 A | 7/2003 |
| CN | 1568158 A | 1/2005 |
| CN | 1627916 A | 6/2005 |
| CN | 1723839 A | 1/2006 |
| CN | 1785117 A | 6/2006 |
| CN | 1931088 A | 3/2007 |
| CN | 101081167 A | 12/2007 |
| CN | 101193588 A | 6/2008 |
| CN | 101288586 A | 10/2008 |
| CN | 101321490 A | 12/2008 |
| CN | 201409913 Y | 2/2010 |
| CN | 101773387 A | 7/2010 |
| CN | 101785666 A | 7/2010 |
| CN | 102038495 A | 5/2011 |
| CN | 102043893 A | 5/2011 |
| CN | 102481127 A | 5/2012 |
| CN | 102697506 A | 10/2012 |
| CN | 103126655 A | 6/2013 |
| CN | 103230267 A | 8/2013 |
| CN | 103230268 A | 8/2013 |
| CN | 103781414 A | 5/2014 |
| CN | 103959060 A | 7/2014 |
| CN | 104055496 A | 9/2014 |
| CN | 104138253 A | 11/2014 |
| CN | 104188639 A | 12/2014 |
| CN | 104352228 A | 2/2015 |
| CN | 104382569 A | 3/2015 |
| CN | 104511150 A | 4/2015 |
| CN | 104665799 A | 6/2015 |
| CN | 104665821 A | 6/2015 |
| CN | 104856661 A | 8/2015 |
| CN | 104873182 A | 9/2015 |
| CN | 204618202 U | 9/2015 |
| CN | 104958064 A | 10/2015 |
| CN | 204708829 U | 10/2015 |
| CN | 105030195 A | 11/2015 |
| CN | 105054918 A | 11/2015 |
| CN | 105078474 A | 11/2015 |
| CN | 204909471 U | 12/2015 |
| CN | 105266828 A | 1/2016 |
| CN | 105361858 A | 3/2016 |
| CN | 105377124 A | 3/2016 |
| CN | 105455797 A | 4/2016 |
| DE | 10243265 A1 | 3/2004 |
| EP | 0872255 A1 | 10/1998 |
| EP | 0875199 A1 | 11/1998 |
| EP | 1057450 A2 | 12/2000 |
| EP | 1150604 A1 | 11/2001 |
| EP | 1334693 A1 | 8/2003 |
| EP | 2759257 A1 | 7/2014 |
| JP | H06-142082 A | 5/1994 |
| JP | H08-229011 A | 9/1996 |
| JP | H08-229012 A | 9/1996 |
| JP | H08-317912 A | 12/1996 |
| JP | H09-220207 A | 8/1997 |
| JP | H10-185639 A | 7/1998 |
| JP | H11-033003 A | 2/1999 |
| JP | H11-128186 A | 5/1999 |
| JP | 2002-224059 A | 8/2002 |
| JP | 2002-536104 A | 10/2002 |
| JP | 2002336210 A | 11/2002 |
| JP | 2003-24310 A | 1/2003 |
| JP | 2003-325465 A | 11/2003 |
| JP | 2004-121865 A | 4/2004 |
| JP | 2004-136105 A | 5/2004 |
| JP | 2004-223271 A | 8/2004 |
| JP | 2004-261452 A | 9/2004 |
| JP | 2005-21619 A | 1/2005 |
| JP | 2005-237472 A | 9/2005 |
| JP | 2005-532111 A | 10/2005 |
| JP | 2006-212218 A | 8/2006 |
| JP | 3820719 B2 | 9/2006 |
| JP | 2007-117591 A | 5/2007 |
| JP | 2008-61824 A | 3/2008 |
| JP | 2008-086568 A | 4/2008 |
| JP | 2008-536545 A | 9/2008 |
| JP | 2010-22689 A | 2/2010 |
| JP | 2010-200901 A | 9/2010 |
| JP | 2011-189080 A | 9/2011 |
| JP | 2012-521223 A | 9/2012 |
| JP | 2012-205673 A | 10/2012 |
| JP | 2013-31568 A | 2/2013 |
| JP | 2013-094222 A | 5/2013 |
| JP | 2013-517908 A | 5/2013 |
| JP | 2013-208140 A | 10/2013 |
| JP | 2014-105 A | 1/2014 |
| JP | 2014-14556 A | 1/2014 |
| JP | 2014000458 A | 1/2014 |
| JP | 2014-18272 A | 2/2014 |
| JP | 2014-171589 A | 9/2014 |
| JP | 2015-100525 A | 6/2015 |
| JP | 2016002119 A | 1/2016 |
| JP | 2016-87003 A | 5/2016 |
| JP | 2017-189511 A | 10/2017 |
| WO | 97/38626 A1 | 10/1997 |
| WO | 99/26529 A1 | 6/1999 |
| WO | 2004/004558 A1 | 1/2004 |
| WO | 2008/001607 A1 | 1/2008 |
| WO | 2009/020114 A1 | 2/2009 |
| WO | 2009/076126 A1 | 6/2009 |
| WO | 2014/171465 A1 | 10/2014 |
| WO | 2015/178439 A2 | 11/2015 |
| WO | 2016/017579 A1 | 2/2016 |
| WO | 2016/018906 A1 | 2/2016 |
| WO | 2018/017425 A1 | 1/2018 |

OTHER PUBLICATIONS

Office Action in the counterpart Japanese Patent Application No. 2018-512086 dated May 26, 2020 (8 pages).

Du Jun, "Blood pressure changes and heart rate variability in sleep apnea at night", Foreign Medical Neurology Neurosurgery, vol. 24, No. 5,1997, pp. 271-272 (2 pages).

Office Action issued in Chinese Application No. 201780022781.6; dated Jul. 13, 2020 (17 pages).

(56) References Cited

OTHER PUBLICATIONS

Office Action issued in Chinese Application No. 201780022529.5; dated Jul. 17, 2020 (20 pages).
Office Action issued in Chinese Application No. 201780022536.5; dated Jul. 27, 2020 (23 pages).
Office Action issued in Chinese Application No. 201780022567.0; dated Jul. 28, 2020 (20 pages).
Extended European Search Report issued in Application No. 17782508.0, dated Sep. 30, 2019 (8 pages).
Extended European Search Report issued in Application No. 17782507.2, dated Sep. 30, 2019 (8 pages).
Extended European Search Report issued in Application No. 17782506.4, dated Oct. 29, 2019 (9 pages).
Extended European Search Report issued in Application No. 17782509.8, dated Nov. 4, 2019 (8 pages).
Extended European Search Report issued in Application No. 17782514.8, dated Nov. 4, 2019 (9 pages).
Extended European Search Report issued in Application No. 17782515.5, dated Nov. 7, 2019 (9 pages).
Extended European Search Report issued in Application No. 17782510.6, dated Nov. 7, 2019 (9 pages).
Extended European Search Report issued in Application No. 17782511.4, dated Nov. 7, 2019 (9 pages).
Extended European Search Report issued in Application No. 17782513.0, dated Nov. 13, 2019 (8 pages).
Extended European Search Report issued in Application No. 17782516.3, dated Nov. 12, 2019 (8 pages).
Office Action issued in Chinese Application No. 201780022566.6; dated Aug. 4, 2020 (19 pages).
Office Action issued in Chinese Application No. 201780022528.0; dated Aug. 31, 2020 (19 pages).
Office Action issued in Chinese Application No. 201780022530.8; dated Oct. 9, 2020 (16 pages).
Office Action issued in Chinese Application No. 201780022568.5; dated Oct. 10, 2020 (22 pages).
Office Action issued in Japanese Application No. 2018-512086; dated Oct. 6, 2020 (5 pages).
P. Boudreau et al. "Circadian Variation of Heart Rate Variability Across Sleep Stages" Sleep, vol. 36, No. 12, 2013 (10 pages).
Q. Han et al. "The Method of Simultaneously Removing Breathing Baseline and High-frequency Noise in Pulse Wave Signal" Chinese Journal of Medical Physics, vol. 31, No. 2 (5 pages).
Extended European Search Report issued in Application No. 17782512.2, dated Jan. 21, 2020 (8 pages).
Notice of Reasons for Refusal issued in Japanese Application No. 2018-512086, dated Feb. 24, 2020 (5 pages).
Office Action issued in Chinese Application No. 201780022565.1; dated Sep. 1, 2020 (25 pages).
Office Action issued in Chinese Application No. 201780022527.6; dated Oct. 10, 2020 (17 pages).
Office Action issued in U.S. Appl. No. 16/092,151; dated Oct. 19, 2020 (18 pages).
Office Action issued in Chinese Application No. 201780022529.5; dated Jan. 5, 2021 (19 pages).
Office Action issued in the counterpart U.S. Appl. No. 16/092,151, dated Mar. 30, 2020 (29 pages).
International Search Report issued in Application No. PCT/JP2017/015274, dated Jun. 20, 2017 (2 pages).
Written Opinion issued in International Application No. PCT/JP2017/015274, dated Jun. 20, 2017, (5 pages).
International Preliminary Report on Patentability issued in Application No. PCT/JP2017/015274, dated Oct. 16, 2018 (6 pages).
International Search Report issued in Application No. PCT/JP2017/015275, dated Jul. 4, 2017 (2 pages).
Written Opinion issued in International Application No. PCT/JP2017/015275, dated Jul. 4, 2017 (7 pages).
International Preliminary Report on Patentability issued in Application No. PCT/JP2017/015275, dated Oct. 16, 2018 (8 pages).
International Search Report issued in Application No. PCT/JP2017/015276, dated Jun. 27, 2017 (2 pages).
Written Opinion issued in International Application No. PCT/JP2017/015276, dated Jun. 27, 2017 (4 pages).
International Preliminary Report on Patentability issued in Application No. PCT/JP2017/015276, dated Oct. 16, 2018 (5 pages).
International Search Report issued in Application No. PCT/JP2017/015277, dated Jul. 18, 2017 (2 pages).
Written Opinion issued in International Application No. PCT/JP2017/015277, dated Jul. 18, 2017 (4 pages).
International Preliminary Report on Patentability issued in Application No. PCT/JP2017/015277, dated Oct. 16, 2018 (5 pages).
International Search Report issued in Application No. PCT/JP2017/015278, dated Jul. 11, 2017 (2 pages).
Written Opinion issued in International Application No. PCT/JP2017/015278, dated Jul. 11, 2017 (4 pages).
International Preliminary Report on Patentability issued in Application No. PCT/JP2017/015278, dated Oct. 16, 2018 (5 pages).
International Search Report issued in Application No. PCT/JP2017/015279, dated Jul. 11, 2017 (1 page).
Written Opinion issued in International Application No. PCT/JP2017/015279, dated Jul. 11, 2017 (4 pages).
International Preliminary Report on Patentability issued in Application No. PCT/JP2017/015279, dated Oct. 16, 2018 (5 pages).
International Search Report issued in Application No. PCT/JP2017/015280, dated Jul. 18, 2017 (2 pages).
Written Opinion issued in International Application No. PCT/JP2017/015280, dated Jul. 18, 2017 (4 pages).
International Preliminary Report on Patentability issued in Application No. PCT/JP2017/015280, dated Oct. 16, 2018 (5 pages).
International Search Report issued in Application No. PCT/JP2017/015281, dated Jul. 18, 2017 (2 pages).
Written Opinion issued in International Application No. PCT/JP2017/015281, dated Jul. 18, 2017 (3 pages).
International Preliminary Report on Patentability issued in Application No. PCT/JP2017/015281, dated Oct. 16, 2018 (4 pages).
International Search Report issued in Application No. PCT/JP2017/015282, dated Jul. 11, 2017 (1 page).
Written Opinion issued in International Application No. PCT/JP2017/015282, dated Jul. 11, 2017 (3 pages).
International Preliminary Report on Patentability issued in Application No. PCT/JP2017/015282, dated Oct. 16, 2018 (4 pages).
International Search Report issued in Application No. PCT/JP2017/015283, dated Jul. 11, 2017 (1 page).
Written Opinion issued in International Application No. PCT/JP2017/015283, dated Jul. 11, 2017 (3 pages).
International Preliminary Report on Patentability issued in Application No. PCT/JP2017/015283, dated Oct. 16, 2018 (4 pages).
International Search Report issued in Application No. PCT/JP2017/015284, dated Jun. 27, 2017 (2 pages).
Written Opinion issued in International Application No. PCT/JP2017/015284, dated Jun. 27, 2017 (3 pages).
International Preliminary Report on Patentability issued in Application No. PCT/JP2017/015284, dated Oct. 16, 2018 (4 pages).
Office Action issued in Chinese Application No. 201780022537.X, dated Feb. 25, 2021 (18 pages).
Office Action issued in Chinese Application No. 201780022567.0, dated Mar. 1, 2021 (16 pages).
Office Action issued in Chinese Application No. 201780022528.0, dated Mar. 2, 2021 (10 pages).
Yigang et al.; "Ventricular Arrhythmias;" Shanghai Jiao Tong University; pp. 258-262 (9 pages).
Guo Dong, Wang Weihua, Li Qingmin, "Three-Hypers" and cardiocerebrovascular disease (M). 2014 (4 pages).
Office Action issued in U.S. Appl. No. 16/092,060, dated Mar. 25, 2021 (50 pages).
McGee; "Evidence-Based Physical Diagnosis;" ScienceDirect; 4th Edition; 2017 (4 pages).
Office Action issued in U.S. Appl. No. 16/092,076; dated Jan. 31, 2022 (15 pages).
Office Action issued in U.S. Appl. No. 16/092,136; dated Jan. 18, 2022 (93 pages).

(56) References Cited

OTHER PUBLICATIONS

Joseph et al., "Slow Breathing Improves Arterial Baroreflex Sensitivity and Decreases Blood Pressure in Essential Hypertension", Aug. 29, 2005, American Heart Association Hypertension, vol. 46, No. 5, pp. 714-718 (5 pages).
Office Action issued in U.S. Appl. No. 16/092,095; dated Jul. 26, 2021 (66 pages).
Office Action issued in U.S. Appl. No. 16/092,167; dated Aug. 3, 2021 (88 pages).
Office Action issued in U.S. Appl. No. 16/092,113; dated Aug. 4, 2021 (94 pages).
W. Hu et al. "Diastolic Blood Pressure Rises with the Exacerbation of Obstructive Sleep Apnea in Males" Obesity, vol. 25, No. 11; Nov. 2017 (9 pages).
Office Action issued in U.S. Appl. No. 16/092,134; dated Jun. 23, 2021 (84 pages).
Office Action issued in U.S. Appl. No. 16/092,076; dated Jun. 28, 2021 (78 pages).
Office Action issued in U.S. Appl. No. 16/092,060; dated Jul. 9, 2021 (30 pages).
Restriction Requirement issued in U.S. Appl. No. 16/092,136; dated Jul. 12, 2021 (7 pages).
Office Action issued in U.S. Appl. No. 16/092,113; dated Feb. 9, 2022 (37 pages).
United States Office Action in related U.S. Appl. No. 16/092,126, dated Jul. 6, 2022 (23 pages).
Office Action issued in U.S. Appl. No. 16/092,060; dated Apr. 14, 2022 (20 pages).
Office Action issued In European Application No. 17782506.4 dated Nov. 9, 2022 (6 pages).

* cited by examiner

BIOLOGICAL INFORMATION ANALYSIS DEVICE, BIOLOGICAL INFORMATION ANALYSIS SYSTEM, PROGRAM, AND BIOLOGICAL INFORMATION ANALYSIS METHOD

TECHNICAL FIELD

The present invention relates to a technique for obtaining useful information from a measured blood pressure waveform.

RELATED ART

Techniques are known in which changes in the internal pressure of the radial artery are measured and the shape of pressure pulses (a blood pressure waveform) is recorded. Patent Document 1 (JP 2008-61824A) discloses measuring a blood pressure waveform through tonometry and obtaining information such as AI (Augmentation Index) value, pulse wave period, baseline fluctuation rate, sharpness, ET (Ejection Time), and the like from the blood pressure waveform. Patent Document 2 (JP 2005-532111A), meanwhile, discloses measuring a blood pressure waveform using a wristwatch-type blood pressure monitor, calculating a mean arterial pressure, a mean systolic pressure, a mean diastolic pressure, a mean systolic pressure index, and a mean diastolic pressure index from the blood pressure waveform, and then outputting an alert when those values deviate from reference values.

RELATED ART DOCUMENTS

Patent Documents

Patent Document 1: JP 2008-61824A
Patent Document 2: JP 2005-532111A

SUMMARY OF THE INVENTION

Problem to be Solved by the Invention

The inventors of the present invention are undertaking diligent research toward putting into practical use blood pressure measurement devices capable of accurately measuring a blood pressure waveform for each heartbeat during free movement. Through experiments using test subjects throughout the course of this development, the inventors of the present invention discovered that many types of useful information can be extracted from blood pressure waveform data measured continuously during free movement.

Accordingly, an object of the present invention is to provide a technique for obtaining novel and useful information on the basis of blood pressure waveform data.

Means for Solving the Problems

To achieve the above-described object, the present invention employs the following configurations.

A biological information analyzing device according to the present invention is a biological information analyzing device including: an indicator extraction unit that extracts an indicator pertaining to a characteristic of a blood pressure waveform using data of the blood pressure waveform obtained by a sensor, which is worn on a user's body and can non-invasively measure the blood pressure waveform for each of heartbeats, continuously measuring the blood pressure waveform; and a processing unit that carries out a process based on the extracted indicator.

Here, the characteristic of the blood pressure waveform preferably includes at least one of a characteristic of the shape of the blood pressure waveform for a single heartbeat, a change in the blood pressure waveform over time, a frequency component of the blood pressure waveform, and a statistical characteristic of the blood pressure waveform in a set section.

Preferably, the indicator extraction unit extracts an indicator pertaining to respiratory and/or circulatory function on the basis of at least one of a characteristic of the shape of the blood pressure waveform for a single heartbeat, a change in the blood pressure waveform over time, a frequency component of the blood pressure waveform, and a statistical characteristic of the blood pressure waveform in a set section.

Specifically, the indicator extraction unit preferably extracts an indicator pertaining to a pulse abnormality on the basis of a pulse wave interval and/or a pulse pressure in the blood pressure waveform for a single heartbeat. When a pulse abnormality occurs, the blood pressure waveform is disturbed, and that effect appears as a change in the pulse wave interval, the pulse pressure, and so on. According to the present invention, time series data of a blood pressure waveform for each heartbeat can be obtained, and thus changes in the pulse wave interval, the pulse pressure, and so on over time can be obtained accurately. It is therefore possible to extract indicators pertaining to pulse abnormalities (e.g., indicators expressing the extent and frequency of pulse abnormality occurrence, an indicator expressing a degree of change from a normal pulse (degree of divergence), and the like) with a high level of reliability.

For example, the indicator extraction unit preferably extracts an indicator pertaining to a pulse abnormality on the basis of a difference between a pulse wave interval in the blood pressure waveform of a single heartbeat and a reference pulse wave interval, a difference between a pulse pressure in the blood pressure waveform of a single heartbeat and a reference pulse pressure, variation in the pulse wave interval in the blood pressure waveforms of a plurality of heartbeats, variation in the pulse pressure in the blood pressure waveforms of a plurality of heartbeats, or a combination of two or more of these. Evaluating a pulse abnormality on the basis of a combination of a plurality of items makes it possible to further increase the reliability of the extracted indicator.

Preferably, the processing unit outputs information indicating a state of the user's pulse on the basis of the extracted indicator. For example, the processing unit may output information indicating that the user's pulse is abnormal in the case where a value of the extracted indicator is a value indicating the occurrence of a pulse abnormality. Presenting such output to the user or a doctor makes it possible to provide information useful in evaluating or diagnosing pulse states.

A biological information analyzing system according to the present invention is a biological information analyzing system including: a sensor, which is worn on a user's body and can non-invasively measure a blood pressure waveform for each of heartbeats; and a biological information analyzing device that analyzes biological information using data of the blood pressure waveform measured continuously by the sensor.

Note that the present invention can also be realized as a biological information analyzing device or system having at least some of the above configurations and functions. The present invention can also be realized as a biological information analyzing method including at least some of the above-described processes, a program that causes a computer to execute the method, or a computer-readable recording medium in which such a program is recorded in a non-transitory manner. The present invention can also be realized by combining the above-described configurations and processes as long as no technical conflicts result.

EFFECTS OF THE INVENTION

According to the present invention, a technique for obtaining novel and useful information on the basis of blood pressure waveform data can be provided.

EMBODIMENTS OF THE INVENTION

A preferred embodiment of the present invention will be described below with reference to the drawings. Note, however, that the descriptions of configurations given hereinafter should be changed as appropriate depending on the configuration of the device to which the invention is applied, various types of conditions, and so on, and the scope of the invention is not intended to be limited by the following descriptions.

Biological Information Analyzing System

Figure 1:
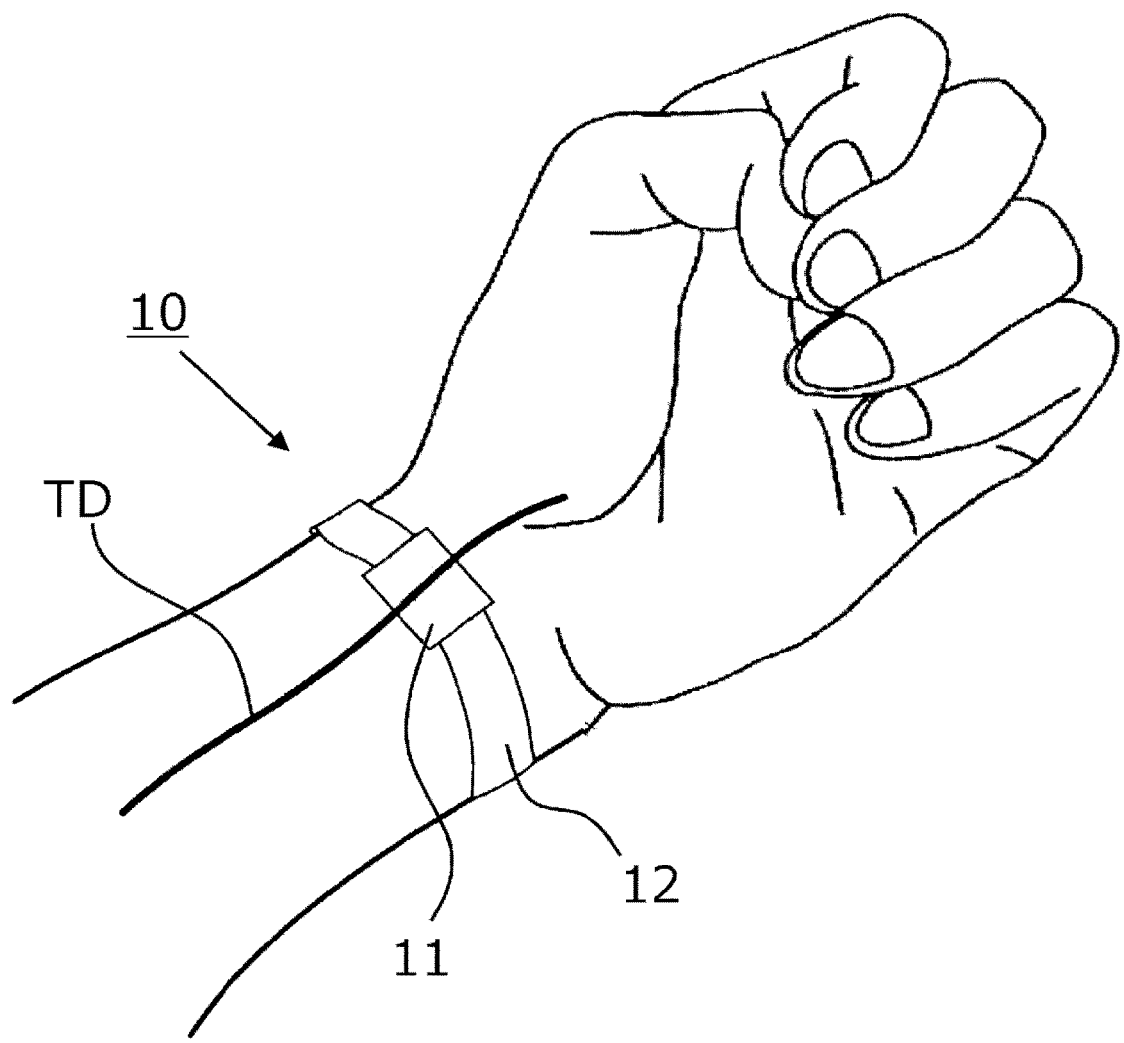
FIG. 1 is a diagram illustrating the external appearance of the overall configuration of a biological information analyzing system 10.

FIG. 1 is a diagram illustrating the external appearance of the overall configuration of a biological information analyzing system 10 according to an embodiment of the present invention. FIG. 1 illustrates a state in which the biological information analyzing system 10 is worn on the left wrist. The biological information analyzing system 10 includes a main unit 11 and a belt 12 fixed to the main unit 11. The biological information analyzing system 10 is what is known as a wearable device, and is worn so that the main unit 11 is in contact with the skin on the inner side of the wrist and so that the main unit 11 is arranged above a radial artery TD located beneath the skin. Although the present embodiment describes a configuration in which the device is worn above the radial artery TD, the configuration may be such that the device is worn above another superficial artery.

Figure 2:
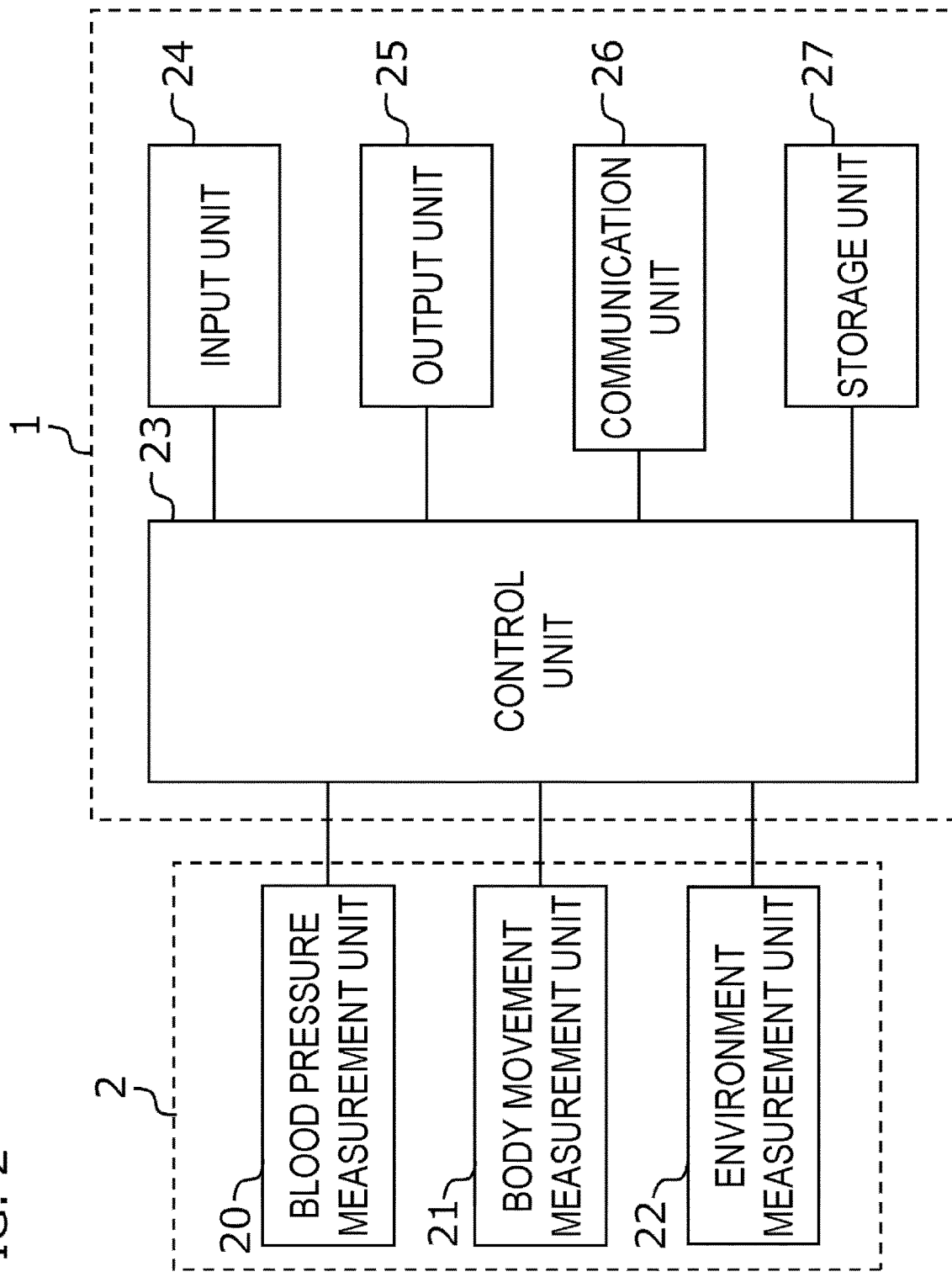
FIG. 2 is a block diagram illustrating the hardware configuration of the biological information analyzing system 10.

FIG. 2 is a block diagram illustrating the hardware configuration of the biological information analyzing system 10. Broadly speaking, the biological information analyzing system 10 includes a measurement unit 2 and a biological information analyzing device 1. The measurement unit 2 is a device that obtains information used to analyze biological information through measurement, and includes a blood pressure measurement unit 20, a body movement measurement unit 21, and an environment measurement unit 22. However, the configuration of the measurement unit 2 is not limited to that illustrated in FIG. 2. For example, units that measure biological information aside from blood pressure and body movement (body temperature, blood sugar, brain waves, and so on) may be added. Alternatively, units not used in the Example described later are not required configurations and may therefore be omitted from the biological information analyzing system 10. The biological information analyzing device 1 is a device that analyzes biological information on the basis of information obtained from the measurement unit 2, and includes a control unit 23, an input unit 24, an output unit 25, a communication unit 26, and a storage unit 27. The units 20 to 27 are connected to each other by a local bus and other signal lines so as to be capable of exchanging signals. The biological information analyzing system 10 also includes a power source (a battery), which is not illustrated.

The blood pressure measurement unit 20 is a unit that measures pressure pulses in the radial artery TD through tonometry. Tonometry is a non-invasive method of measuring pressure pulses using a pressure sensor, in which an artery is compressed from above the skin at an appropriate pressure to form a flat part in an artery TD, and the internal pressure and external pressure of the artery are balanced.

The body movement measurement unit 21 is a unit, including a three-axis accelerometer, that measures movement of a user's body (body movement) using the accelerometer. The body movement measurement unit 21 may include a circuit that converts the output of the three-axis accelerometer into a format that can be read by the control unit 23.

The environment measurement unit 22 is a unit that measures environment information that can affect the user's physical/mental state (and blood pressure in particular). The environment measurement unit 22 can include a temperature sensor, a humidity sensor, an illuminance sensor, an altitude sensor, a location sensor, and the like, for example. The environment measurement unit 22 may include a circuit that converts the output of these sensors into a format that can be read by the control unit 23.

The control unit 23 is a unit that handles a variety of processes, such as controlling the various parts of the biological infoiniation analyzing system 10, acquiring data from the measurement unit 2, storing the acquired data in the storage unit 27, processing/analyzing the data, inputting/outputting the data, and so on. The control unit 23 includes a hardware processor (called a CPU hereinafter), ROM (Read-Only Memory), RAM (Random Access Memory), and the like. The processing carried out by the control unit 23, which will be described later, is realized by the CPU reading programs stored in the ROM or the storage unit 27 and executing those programs. The RAM functions as a work memory when the control unit 23 carries out various types of processes. Although the present embodiment describes a configuration in which the control unit 23 acquires the data from the measurement unit 2 and stores the data in the storage unit 27, the configuration may be such that the data is stored (written) directly from the measurement unit 2 into the storage unit 27.

The constituent elements of the embodiment, e.g., the measurement units, an indicator extraction unit, a processing unit, a determination unit, a risk database, the input unit, the output unit, a case database, and the like may be provided as hardware in the biological information analyzing system 10. The indicator extraction unit, the processing unit, and the determination unit may receive executable programs stored in the storage unit 27 and execute those programs. The indicator extraction unit, the processing unit, and the determination unit may receive data from the blood pressure measurement unit 20, the body movement measurement unit 21, the environment measurement unit 22, the input unit 24, the output unit 25, the communication unit 26, the storage unit 27, and so on as necessary. Databases such as the risk database and the case database may be provided in the storage unit 27 or the like, and may store information arranged so that the data can be searched and accumulated with ease. The structure, operations, and the like of the biological information analyzing system 10 are disclosed in JP 2016-082069, for example. The content thereof is incorporated into this specification by reference. The structure, operations, and the like of the blood pressure measurement unit are disclosed in JP 2016-087003A. The content thereof is incorporated into this specification by reference.

The input unit 24 is a unit that provides an operation interface to the user. For example, operation buttons, switches, a touch panel, or the like can be used.

The output unit 25 is a unit that provides, to the user, an interface that outputs information. For example, a display device that outputs information as images (a liquid crystal display or the like), an audio output device or a buzzer that outputs information as audio, an LED that outputs information by emitting or extinguishing light, a vibration device that outputs information as vibrations, or the like can be used.

The communication unit 26 is a unit that carries out data communication with other devices. Any system, including wireless LAN, Bluetooth (registered trademark), or the like, may be used as the data communication system.

The storage unit 27 is a storage medium in which data can be stored and from which data can be read out, and stores programs executed by the control unit 23, measurement data obtained from the measurement units, various types of data obtained by processing the measurement data, and so on. The storage unit 27 is a medium that electrically, magnetically, optically, mechanically, or chemically stores the information to be stored. Flash memory can be used, for example. The storage unit 27 may be a portable type such as a memory card, or may be built into the biological information analyzing system 10.

Some or all of the body movement measurement unit 21, the environment measurement unit 22, the control unit 23, the input unit 24, the output unit 25, and the storage unit 27 may be configured as devices separate from the main unit 11. In other words, as long as the main unit 11 including the blood pressure measurement unit 20 and a circuit that controls the blood pressure measurement unit 20 can be worn on a wrist, the structures of other units can be designed as desired. In this case, the main unit 11 is linked to the other units via the communication unit 26. A variety of configurations are conceivable, such as implementing the functions of the control unit 23, the input unit 24, the output unit 25, and so on as a smartphone app, or obtaining necessary data from an activity meter having the functions of the body movement measurement unit 21, the environment measurement unit 22, and so on. Sensors that measure biological information aside from blood pressure may be provided as well. For example, a sleep sensor, a pulse oximeter (SpO2 sensor), a breathing sensor (flow sensor), a blood sugar level sensor, and so on may be combined as well.

Although the present embodiment describes providing a sensor that measures blood pressure (the blood pressure measurement unit 20) and a configuration that carries out analysis processes on blood pressure waveform data (the control unit 23 and the like) in a single device, these elements may be configured as separate entities. In the present embodiment, a configuration that carries out analysis processes on biological information (the control unit 23 and the like) is called a "biological information analyzing device", and a device configured by combining a measurement unit and the biological information analyzing device is called a "biological information analyzing system". However, these names are used for the sake of simplicity, and the measurement unit and the configuration that carries out analysis processes on biological information may as a whole be called a "biological information analyzing device", or other names may be used instead.

Blood Pressure Waveform Measurement

Figure 3:
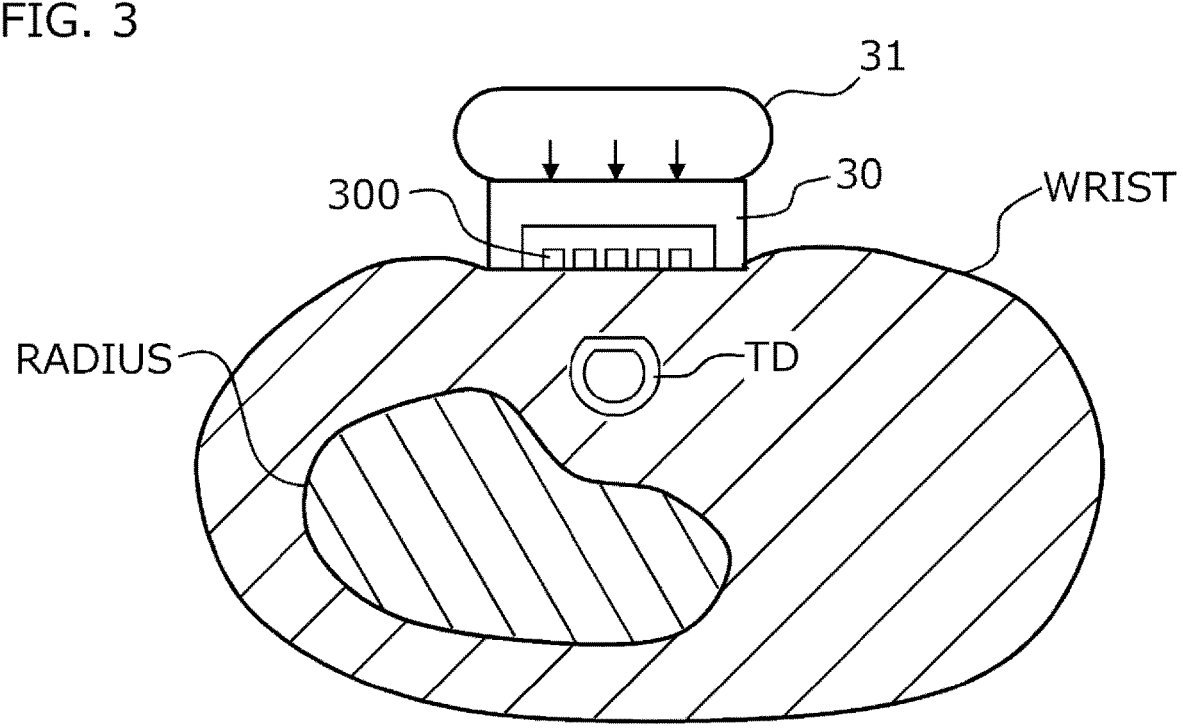
FIG. 3 is a cross-sectional view schematically illustrating the structure of a blood pressure measurement unit 20 and a measurement state.

FIG. 3 is a cross-sectional view schematically illustrating the structure of the blood pressure measurement unit 20 and a measurement state. The blood pressure measurement unit 20 includes a pressure sensor 30, and a compression mechanism 31 for pressing the pressure sensor 30 against the wrist. The pressure sensor 30 includes a plurality of pressure detection elements 300. The pressure detection elements 300 are elements that detect a pressure and convert the pressure into an electrical signal, and elements that use a piezoresistance effect, for example, can be favorably used. The compression mechanism 31 is constituted by, for example, an air bladder and a pump that adjusts the internal pressure of the air bladder. When the control unit 23 controls the pump to increase the internal pressure of the air bladder, the air bladder expands and presses the pressure sensor 30 against the surface of the skin. Note that the compression mechanism 31 may be any mechanism capable of adjusting a compressive force of the pressure sensor 30 against the surface of the skin, and is not limited to a mechanism employing an air bladder.

When the biological information analyzing system 10 is secured to the wrist and started, the control unit 23 controls the compression mechanism 31 of the blood pressure measurement unit 20 to keep the compressive force of the pressure sensor 30 in an appropriate state (a tonometry state). Pressure signals detected by the pressure sensor 30 are then acquired sequentially by the control unit 23. The pressure signals obtained by the pressure sensor 30 are generated by taking analog physical amounts (e.g., voltage values) outputted by the pressure detection elements 300 and digitizing those physical amounts through an A/D conversion circuit or the like that employs a known technique. Suitable analog values such as current values, resistance values, or the like may be employed as the analog physical amounts, depending on the types of the pressure detection elements 300. The signal processing such as A/D conversion may be carried out by providing a predetermined circuit in the blood pressure measurement unit 20, or may be carried out by another unit (not shown) provided between the blood pressure measurement unit 20 and the control unit 23. The pressure signals acquired by the control unit 23 correspond to instantaneous values of the internal pressure of the radial artery TD. Accordingly, time series data of a blood pressure waveform can be obtained by acquiring a pressure signal at a time granularity and continuity that enable the blood pressure waveform of a single heartbeat to be obtained. The control unit 23 stores the pressure signals sequentially obtained from the pressure sensor 30 in the storage unit 27 along with information of the measurement times of the signals. The control unit 23 may store the acquired pressure signals as-is in the storage unit 27, or may store the pressure signals in the storage unit 27 after applying necessary signal processing to the pressure signals. The "necessary signal processing" may include processing for correcting the pressure signals so that the amplitude of the pressure signals matches a blood pressure value (e.g., an upper arm blood pressure), processing for reducing or removing noise from the pressure signals, or the like, for example.

Figure 4:
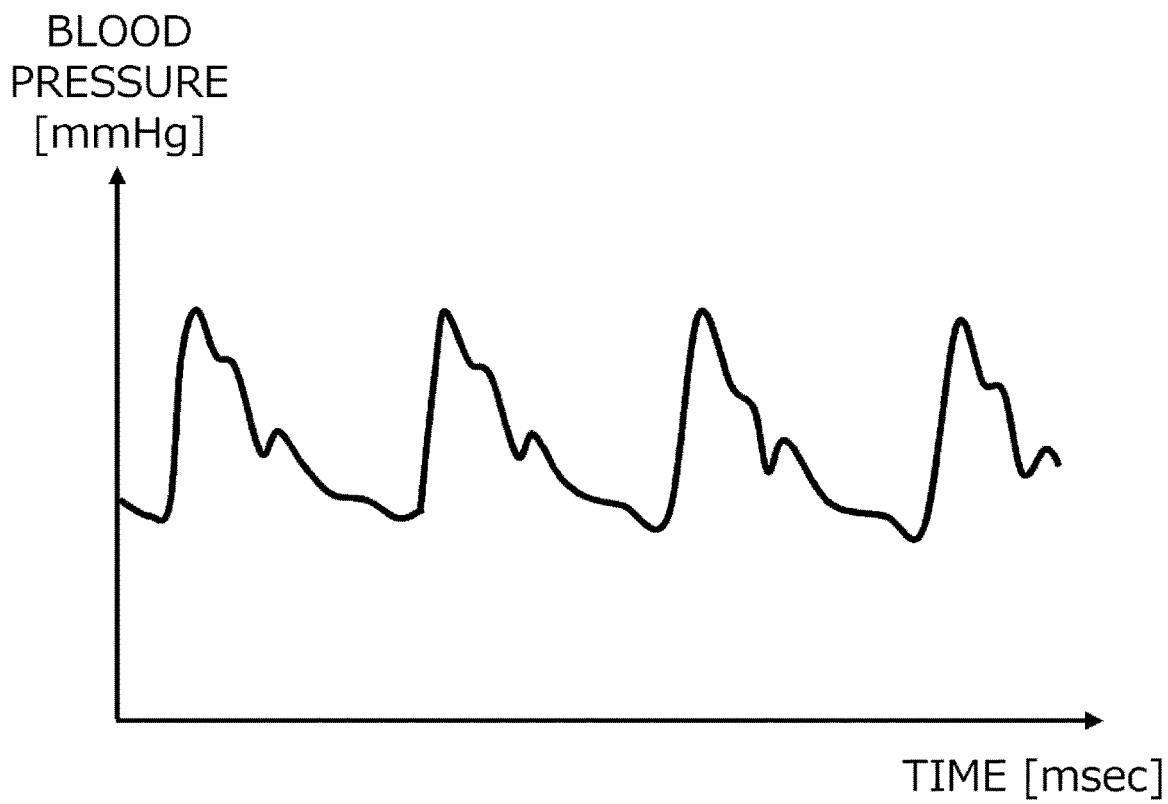
FIG. 4 is a diagram illustrating a blood pressure waveform measured by the blood pressure measurement unit 20.

FIG. 4 is a diagram illustrating a blood pressure waveform measured by the blood pressure measurement unit 20. The horizontal axis represents time, and the vertical axis represents blood pressure. The sampling frequency can be set as desired, but is preferably set to greater than or equal to 100 Hz in order to reproduce the shape characteristics of the waveform of a single heartbeat. Because the period of a single heartbeat is approximately one second, approximately 100 or more data points can be acquired in the waveform of a single heartbeat.

The blood pressure measurement unit 20 according to the present embodiment has advantages such as those described below.

A blood pressure waveform can be measured for each heartbeat. Thus for example, a variety of indicators related to blood pressure, heart condition, cardiovascular risk, and so on can be obtained on the basis of the shape characteristics of the blood pressure waveform. Additionally, the instantaneous value of the blood pressure can be monitored, which makes it possible to immediately detect blood pressure surges (sudden rises in blood pressure value), reliably detect blood pressure fluctuations and disturbances in the blood pressure waveform appearing only over extremely short amounts of time (one to several heartbeats), and so on.

Blood pressure monitors that are secured to the wrist or upper arm and measure blood pressure through the oscillometric method are in practical use as portable blood pressure monitors. However, a conventional portable blood pressure monitor can only measure a mean blood pressure value from fluctuations in the internal pressure of a cuff over several heartbeats, spanning several seconds to several tens of seconds, and thus cannot obtain time series data of a blood pressure waveform for each heartbeat, as is the case with the blood pressure measurement unit 20 according to the present embodiment.

The blood pressure waveform time series data can be recorded. When the blood pressure waveform time series data is acquired, a variety of indicators pertaining to blood pressure, heart condition, cardiovascular risk, and the like can be obtained by finding characteristics pertaining to changes in the blood pressure waveform over time, analyzing the frequency of the time series data and extracting specific frequency components, and so on, for example.

Because the device is configured as a portable (wearable) device, measurements place little burden on the user, and it is relatively easy to take continuous measurements for long periods of time, monitor blood pressure throughout the entire day, and so on. Furthermore, the portable form makes it possible not only to measure resting blood pressure, but also to measure changes in blood pressure during free movement (e.g., during daily activities, exercise, and so on). This in turn makes it possible to understand the effects of daily activities (sleeping, meals, commuting, work, taking medicine, and so on), exercise, and so on on blood pressure, for example.

Conventional products are devices of a type in which a blood pressure measurement unit is secured to the arm or wrist and the measurement is taken in a state of rest, and changes in blood pressure during daily activities, exercise, and so on cannot be measured, as with the biological information analyzing system 10 according to the present embodiment.

It is easy to link or combine the system with other sensors. For example, causal relationship evaluations or compound evaluations can be made using information obtained from other sensors (body movement, environment information such as temperature, other biological information such as SpO2 or breathing, and the like).

Biological Information Analyzing Device

Figure 5:
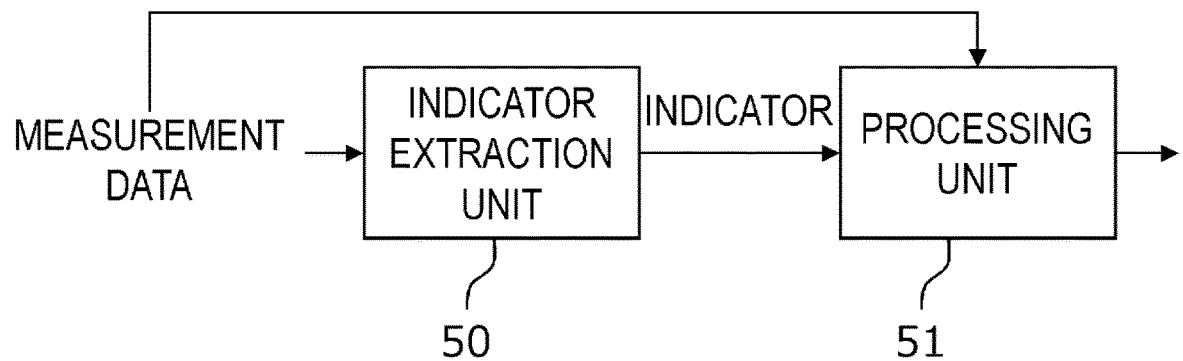
FIG. 5 is a block diagram illustrating processing performed by a biological information analyzing device 1.

FIG. 5 is a block diagram illustrating processing performed by the biological information analyzing device 1. As illustrated in FIG. 5, the biological information analyzing device 1 includes an indicator extraction unit 50 and a processing unit 51. In the present embodiment, the processes of the indicator extraction unit 50 and the processing unit 51 may be realized by the control unit 23 executing necessary programs. These programs may be stored in the storage unit 27. When executing the necessary programs, the control unit 23 loads the programs in question, which are stored in the ROM or the storage unit 27, into the RAM. The control unit 23 then uses a CPU to interpret and execute the programs loaded into the RAM, and controls the various constituent elements. However, some or all the processing of the indicator extraction unit 50 and the processing unit 51 may be implemented by a circuit such as an ASIC, a FPGA, or the like. Alternatively, some or all of the processing of the indicator extraction unit 50 and the processing unit 51 may be implemented by a computer separate from the main unit 11 (e.g., a smartphone, a tablet terminal, a personal computer, a cloud server, or the like).

The indicator extraction unit 50 obtains, from the storage unit 27, the blood pressure waveform time series data measured continuously by the blood pressure measurement unit 20. The indicator extraction unit 50 extracts an indicator pertaining to characteristics of the blood pressure waveform, from the obtained blood pressure waveform time series data. Here, "characteristics of the blood pressure waveform" include shape characteristics of the blood pressure waveform for a single heartbeat, changes in the blood pressure waveform over time, a frequency component of the blood pressure waveform, and so on. The blood pressure waveform characteristics are not limited thereto, however. The extracted indicator is output to the processing unit 51. Because there are a variety of blood pressure waveform characteristics and indicators, the characteristics and indicators to be extracted can be designed and selected as appropriate in accordance with the purpose of the processing by the processing unit 51. The characteristics and indicators that can be extracted from the blood pressure waveform measurement data in the present embodiment will be described later.

When finding the indicator, the indicator extraction unit 50 can use the measurement data from the body movement measurement unit 21 and/or the measurement data from the environment measurement unit 22 in addition to the blood pressure waveform measurement data. Although not illustrated, measurement data from a sleep sensor, an SpO2 sensor, a breathing sensor (flow sensor), a blood sugar level sensor, or the like may be combined as well. Carrying out a compound analysis on multiple types of measurement data obtained from multiple types of sensors enables a higher level of information analysis to be carried out on the blood pressure waveform. For example, the blood pressure waveform data can be classified into user states, such as resting and active, times of high and low temperature, times of light and deep sleep, breathing and apnea, and so on. Alternatively, causal relationships, correlations, and so on among the measurement data can be evaluated, by extracting the effects of body movement, activity amounts and activity intensity, changes in temperature, how breathing or apnea manifests, and so on blood pressure. Note that apnea includes obstructive apnea, central apnea, and mixed apnea.

The processing unit 51 receives the indicator extracted by the indicator extraction unit 50. The processing unit 51 carries out processing on the basis of the received indicator. A variety of processes are conceivable as the processes based on the indicator. For example, values of or changes in the extracted indicator may be provided to the user, a doctor, a nurse, or the like and used for health management, treatment, health guidance, and so on. Alternatively, circulatory system risk may be predicted, guidelines for maintaining one's health or reducing risks may be provided, or the like, on the basis of the extracted indicator. Furthermore, if a rise in cardiovascular risk has been detected or predicted on the basis of the indicator, the user or an attending doctor may be notified, control may be carried out to prevent activity that will place an excessive burden on the user's heart or prevent the occurrence of the circulatory system event, and so on.

Information Obtained from Blood Pressure Waveform

Figure 6:
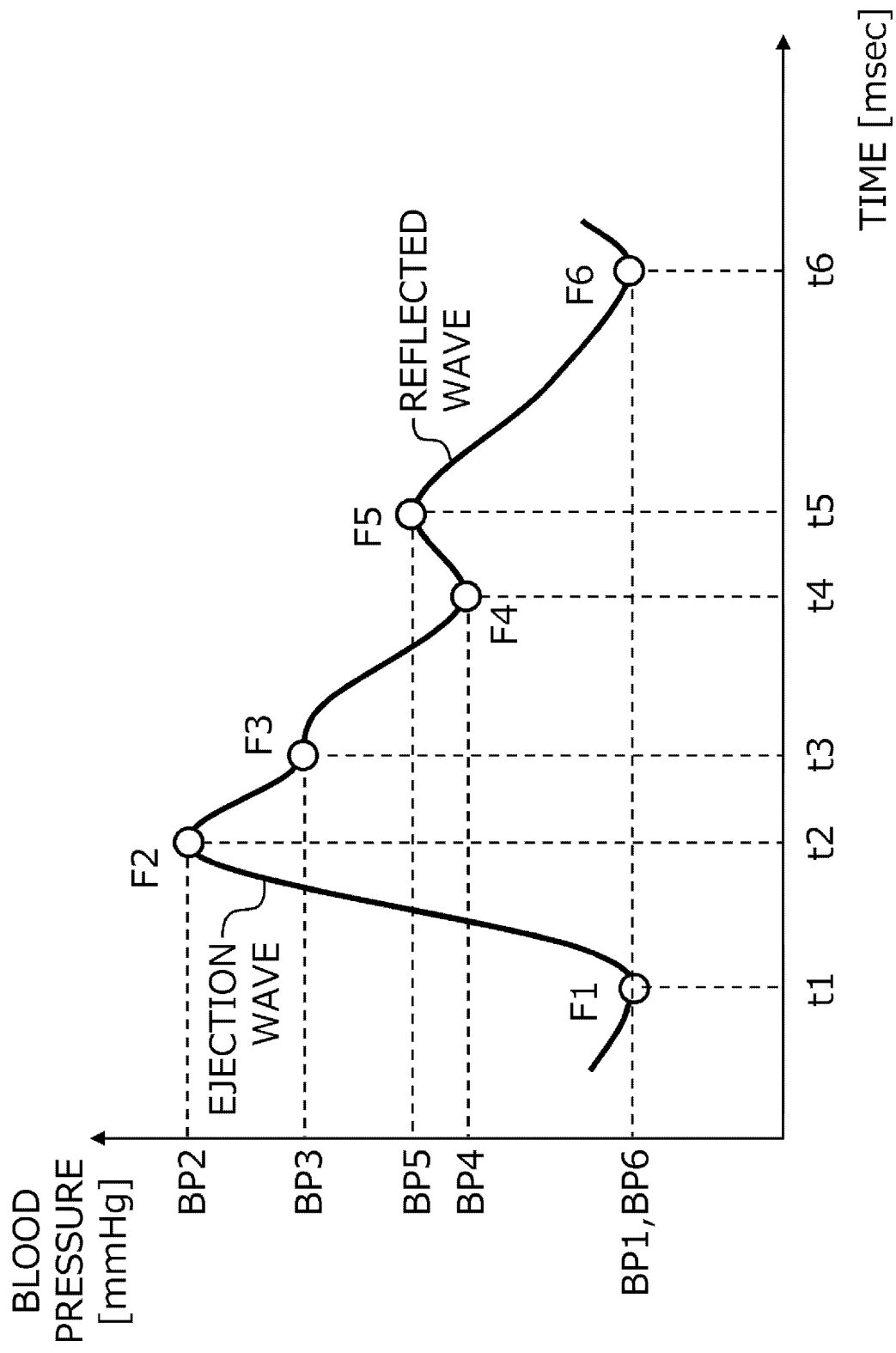
FIG. 6 is a diagram illustrating the waveform of a pressure pulse (a blood pressure waveform) in the radial artery, for a single heartbeat.

FIG. 6 is a diagram illustrating the waveform of a pressure pulse (a blood pressure waveform) in the radial artery, for a single heartbeat. The horizontal axis represents time t [in-sec], and the vertical axis represents blood pressure BP [mmHg].

The blood pressure waveform is a compound wave including an "ejection wave" produced when the heart contracts to expel blood and a "reflected wave" produced when the ejection wave is reflected by peripheral vessels, arterial branches, and so on. Examples of characteristic points that can be extracted from a blood pressure waveform corresponding to a single heartbeat are listed below.

Point F1 is a point corresponding to the rise of the pressure pulse. The point F1 corresponds to an ejection start point of the heart, i.e., a point when the aortic valve opens.

Point F2 is a point where the amplitude (pressure) of the ejection wave is maximum (a first peak).

Point F3 is an inflection point appearing partway along the fall of the ejection wave due to the superposition of the reflected wave.

Point F4 is a minimum point appearing between the ejection wave and the reflected wave, and is also called a "notch". This corresponds to a point when the aortic valve closes.

Point F5 is a peak in the reflected wave appearing after point F4 (a second peak).

Point F6 is the end point of the single heartbeat, and corresponds to the ejection start point of the next heartbeat, i.e., the starting point of the next heartbeat.

The indicator extraction unit 50 may use any algorithm to detect the characteristic points. For example, the indicator extraction unit 50 may extract a characteristic point (inflection point) of the blood pressure waveform by operating so as to find a nth-order differential waveforms of the blood pressure waveform and detect a zero crossing point thereof (for points F1, F2, F4, F5, and F6, this can be detected from a first-order differential waveform, and for point F3, from a second-order or fourth-order waveform). Alternatively, the indicator extraction unit 50 may identify the positions of the characteristic points by reading out a waveform pattern, in which characteristic points have been arranged in advance, from the storage unit 27, and fitting the blood pressure waveform in question to the waveform pattern.

By operating on the basis of the times t and the pressures BP of the above characteristic points F1 to F6, the indicator extraction unit 50 can obtain a variety of information (values, feature amounts, indicators, and the like) from the blood pressure waveform of a single heartbeat. The following provides representative examples of information that can be obtained from the blood pressure waveform. Note that tx and BPx represent the time and blood pressure, respectively, of a characteristic point Fx.

pulse wave interval (heartbeat period) TA=t6−t1
heart rate PR=1/TA
pulse wave rise time UT=t2−t1
systole TS=t4−t1
diastole TD=t6−t4
reflected wave delay time=t3−t1
maximum blood pressure (systolic blood pressure) SBP=BP2
minimum blood pressure (diastolic blood pressure) DBP=BP1
mean blood pressure MAP=area of blood pressure waveform from t1 to t6/heartbeat period TA
systolic mean blood pressure=area of blood pressure waveform from t1 to t4/systole TS
diastolic mean blood pressure=area of blood pressure waveform from t4 to t6/diastole TD
pulse pressure PP=maximum blood pressure SBP−minimum blood pressure DBP
late systolic pressure SBP2=BP3
AI (Augmentation Index)=(late systolic pressure SBP2−minimum blood pressure DBP)/pulse pressure PP Basic statistical amounts of this information (values, feature amounts, indicators) can also be used as indicators. The basic statistical amounts include representative values (mean values, median values, mode values, maximum values, minimum values, and the like) and dispersion (variance, standard deviation, coefficient of variation, and the like), for example. Changes over time in this information (values, characteristic values, indicators) can also be used as indicators.

By computing a plurality of pieces of beat information, the indicator extraction unit 50 can obtain an indicator called BRS (baroreflex sensitivity). This is an indicator expressing the capacity of blood pressure to regulate to a constant value. The spontaneous sequence method is an example of the calculation method. This is a method in which only a sequence in which the maximum blood pressure SBP and the pulse wave interval TA rise or fall in synchronization for three or more consecutive beats is extracted, the maximum blood pressure SBP and the pulse wave interval TA are plotted on a two-dimensional plane, and a slope obtained when a regression line is found through the least-squares method is defined as the BRS.

Furthermore, the indicator extraction unit 50 can calculate information such as that described below by computing the blood pressure waveform time series data for each heartbeat.

When a pulse abnormality occurs, the blood pressure waveform is disturbed, and that effect appears as a change in the pulse wave interval (TA), the pulse pressure (PP), and so on. Accordingly, the indicator extraction unit 50 can find an indicator pertaining to the pulse abnormality on the basis of changes over time in the pulse wave interval and/or pulse pressure in a blood pressure waveform for a single heartbeat. For example, the indicator extraction unit 50 may find an indicator pertaining to a pulse abnormality on the basis of a difference between the pulse wave interval in the blood pressure waveform of a single heartbeat and a reference pulse wave interval, the difference between a pulse pressure in the blood pressure waveform of a single heartbeat and a reference pulse pressure, variation in the pulse wave interval in the blood pressure waveforms of a plurality of heartbeats, variation in the pulse pressure in the blood pressure waveforms of a plurality of heartbeats, or a combination of two or more of these.

Additionally, the indicator extraction unit 50 may extract indicators on the basis of predetermined frequency components included in the time series data of the blood pressure waveform. When the time series data of the blood pressure waveform is converted into a frequency spectrum, features that cannot be known from the blood pressure waveform (the original waveform) sometimes appear. Through experimentation, the inventors of the present invention discovered that a predetermined frequency component in the frequency spectrum increases significantly when apnea occurs during the measurement of the blood pressure waveform, when a part of the body is moved during the measurement of the blood pressure waveform, and the like. Thus for example, by performing computations to convert the time series data of the blood pressure waveform into a frequency spectrum and then evaluate the strength of the predetermined frequency component, the indicator extraction unit 50 can calculate indicators pertaining to the function of the respiratory organs and/or circulatory organs, detect body movement of the user during measurement, and so on. Experiments will likely also clarify the relationship between other user behavior, conditions, and events, and the frequency spectrum of the blood pressure waveform. User body movement during measurement may reduce the reliability of the measurement data, and thus it is also possible to obtain an indicator expressing the reliability of the measurement data on the basis of the strength of the frequency component corresponding to the user's body movement.

The indicator extraction unit 50 may extract, from the blood pressure waveform data, blood pressure waveform data in a resting section and blood pressure waveform data in an active section, and may find an indicator on the basis of a difference between the blood pressure waveform in the resting section and the blood pressure waveform in the active section. The resting section is a section in which the user is at rest, and the active section is a section in which the user is active. Whether a section is a resting section or an active section may be input (taught) by a person using the input unit 24. Alternatively, the biological information analyzing device 1 may be provided with a determination unit that determines whether the user is at rest or active on the basis of the blood pressure waveform data and/or the output of a second sensor (the body movement measurement unit 21, the environment measurement unit 22, or the like), and the indicator extraction unit 50 may automatically judge whether a section is a resting section or an active section on the basis of the determination result from the determination unit.

For example, the indicator extraction unit 50 may obtain a time at which the effect of user activity appears as a change in the blood pressure waveform (called an "effect appearance point"), and may find an indicator on the basis of the amount of time that has passed from the start of the activity to the effect appearance point. The indicator extraction unit 50 may calculate an indicator on the basis of a difference in minimum blood pressure values between the blood pressure waveform in the resting section and the blood pressure waveform in the active section. The indicator extraction unit 50 may also calculate an indicator on the basis of a degree of similarity between the shapes of the blood pressure waveform in the resting section and the blood pressure waveform in the active section. Alternatively, an indicator obtained by combining a plurality of types of such indicators may be defined. The indicators described here can be called indicators expressing the load placed on the user's heart by the activities performed by the user in the active section. The activities performed by the user in the active section can be detected by the second sensor (the body movement measurement unit 21 or the like), for example.

The indicator extraction unit 50 may obtain, from the blood pressure waveform data, data of the blood pressure waveform in a blood pressure fluctuation section, which is a section where the blood pressure fluctuates, and find an indicator on the basis of the blood pressure waveform in the blood pressure fluctuation section. This is an indicator of the ways in which blood pressure fluctuates from person to person, and how risk levels differ accordingly. For example, using the second sensor that detects the user's state (the body movement measurement unit 21, the environment measurement unit 22, or the like) and a risk database storing user states and event occurrence risks in association with each other, the indicator extraction unit 50 may use the information obtained from the second sensor during a time corresponding to the blood pressure fluctuation section to estimate the cause of the blood pressure fluctuations in the blood pressure fluctuation section, and then find the event occurrence risk of the user on the basis of the estimation result and the risk database. Additionally, characteristics of the user's blood pressure waveform may be classified into groups, and using a risk database storing those classifications in association with event occurrence risks, the indicator extraction unit 50 may create group classifications on the basis of the characteristics of the blood pressure waveform in the blood pressure fluctuation section, and find the user's event occurrence risk on the basis of the classification result and the risk database. Furthermore, if the risk database stores user attribute information (sex, age, and the like) in association with event occurrence risks, it is preferable that the indicator extraction unit 50 accept the user attribute information and find the user's event occurrence risk on the basis of the user attribute information. The risk database is provided at least partially in the storage unit 27, for example.

Experiments by the inventors of the present invention confirmed that disturbances in the blood pressure waveform arise due to changes in the states of respiratory organs, circulatory organs, and so on; specifically, that significant changes are found in the difference between systolic blood pressure and diastolic blood pressure (BP2−BP1), the difference between the minimum value appearing after the systolic blood pressure and the diastolic blood pressure (BP4−BP1), the difference between the maximum value appearing after the minimum value and the diastolic blood pressure (BP5–BP1), and the like. Accordingly, the indicator extraction unit 50 can calculate the difference between the systolic blood pressure and the diastolic blood pressure (BP2–BP1), the difference between the minimum value appearing after the systolic blood pressure and the diastolic blood pressure (BP4–BP1), and the difference between the maximum value appearing after the minimum value and the diastolic blood pressure (BP5–BP1), in the blood pressure waveform of a single heartbeat, and then extract indicators pertaining to the functions of the respiratory organs and/or circulatory organs on the basis of one or more of those values. For example, an indicator expressing the occurrence of apnea can be found.

Additionally, the indicator extraction unit 50 can find an indicator expressing an event occurrence risk due to blood pressure fluctuations on the basis of a difference between the AI in the blood pressure waveform and a reference AI, a difference between the BRS in the blood pressure waveform and a reference BRS, or on the basis of both those values. The indicator extraction unit 50 can also find an indicator expressing the risk for user cases on the basis of characteristics pertaining to an AI and/or BRS distribution in the blood pressure waveform for several heartbeats. The maximum blood pressure SBP, the minimum blood pressure DBP, or the like may be used instead of AI or BRS.

It is preferable that a case database defining trends of characteristics pertaining to the AI and/or BRS distribution for several heartbeats be provided on a case-by-case basis. The indicator extraction unit 50 can compute a degree of similarity between the characteristics pertaining to the user's AI and/or BRS distribution for several heartbeats calculated by the indicator extraction unit 50, and the characteristics of each case stored in the storage unit 27, for example, and then find an indicator expressing that user's risk for the case on the basis of the computation result.

On the basis of the SBP, AI, and BRS calculated on the basis of a current blood pressure waveform measured by the blood pressure measurement unit 20, the indicator extraction unit 50 can predict a blood pressure fluctuation for a case where a blood pressure surge occurs at the present time, and obtain, on the basis of the prediction result, an indicator expressing the event occurrence risk caused by the blood pressure fluctuation.

The indicator extraction unit 50 can find an indicator expressing cardiovascular risk on the basis of characteristics pertaining to a cardiac ejection volume (SV) distribution calculated from the blood pressure waveform of several heartbeats measured by the blood pressure measurement unit 20. For example, the indicator extraction unit 50 can calculate the frequency at which an instantaneous cardiac ejection volume exceeds a first threshold in the cardiac ejection volume (SV) distribution in the blood pressure waveform for several heartbeats, and find an indicator expressing the risk of cardiac enlargement. The indicator extraction unit 50 can also calculate the frequency at which the instantaneous cardiac ejection volume drops below a second threshold in the cardiac ejection volume (SV) distribution in the blood pressure waveform for several heartbeats, and find an indicator expressing the risk of cardiac thrombosis. The indicator extraction unit 50 can also find an indicator expressing the risk of cardiac enlargement on the basis of the maximum value of the instantaneous cardiac ejection volume in the cardiac ejection volume (SV) distribution in the blood pressure waveform for several heartbeats.

The indicator extraction unit 50 can find an indicator expressing cardiovascular risk on the basis of characteristics pertaining to a total peripheral vessel resistance (TPR) distribution in the blood pressure waveform for several heartbeats. For example, the indicator extraction unit 50 can find an indicator expressing the risk of cardiac enlargement on the basis of the frequency at which the value of the total peripheral vessel resistance (TPR) exceeds a first threshold in the total peripheral vessel resistance (TPR) distribution in the blood pressure waveform for several heartbeats. The indicator extraction unit 50 can find an indicator expressing the risk of occurrence pertaining to a time span in which the value of the total peripheral vessel resistance (TPR) changes in the total peripheral vessel resistance (TPR) distribution in the blood pressure waveform for several heartbeats. For example, on the basis of a time span in which the value of the total peripheral vessel resistance changes in the total peripheral vessel resistance distribution in the blood pressure waveform for several heartbeats, the indicator extraction unit 50 can find an indicator expressing the risk of respiratory disorders such as sleep apnea, an indicator expressing the temperature sensitivity of blood pressure, and so on.

Using data of the blood pressure waveform in a section where the blood pressure fluctuates, the indicator extraction unit 50 can determine whether or not the blood pressure fluctuation in that section is caused by apnea, on the basis of a relationship between increases/decreases in heart rate and increases/decreases in systolic blood pressure. If the occurrence of blood pressure fluctuations caused by apnea can be identified in this manner, the indicator extraction unit 50 can find an indicator expressing event occurrence risk on the basis of the frequency at which blood pressure fluctuations occur due to apnea. Additionally, the indicator extraction unit 50 can find an indicator expressing event occurrence risk on the basis of the amount of blood pressure fluctuation caused by apnea.

The indicator extraction unit 50 can divide the blood pressure waveform data into a plurality of sections based on inhalation and exhalation, and can then find an indicator expressing the relationship between breathing and blood pressure on the basis of changes in the blood pressure waveform between before and after each of the sections. The indicator extraction unit 50 can also divide the blood pressure waveform data into a plurality of sections based on inhalation and exhalation, and can then find an indicator expressing the relationship between breathing and blood pressure on the basis of changes in the blood pressure waveform within each of the sections. Here, "changes in the blood pressure waveform" includes at least one of changes in the systolic blood pressure, changes in the diastolic blood pressure, and changes in the AI. Additionally, the indicator extraction unit 50 can divide the blood pressure waveform time series data into a plurality of sections based on inhalation and exhalation, and can then find an indicator expressing the relationship between breathing and blood pressure on the basis of changes in the number of blood pressure surges or changes in a blood pressure search fluctuation amount between before and after each of the sections.

The indicator extraction unit 50 can obtain, from the blood pressure waveform data, blood pressure waveform data in a pre-exercise section corresponding to before the user exercises and blood pressure waveform data in a post-exercise section corresponding to after the user has exercised, and can then find an indicator expressing the effect of the exercise on the user's cardiac function on the basis of a difference (DF) between the characteristics of the blood pressure waveform in the pre-exercise section and the characteristics of the blood pressure waveform in the post-exercise section. The indicator extraction unit 50 can also obtain, from the blood pressure waveform time series data, blood pressure waveform data in the pre-exercise section corresponding to before the user exercises and blood pressure waveform data in the post-exercise section corresponding to after the user has exercised, and can then find an indicator expressing the effect of the exercise on the user's cardiac function on the basis of a time (T) until the characteristics of the blood pressure waveform, which have changed due to the exercise, return to the state found in the pre-exercise section. The indicator extraction unit 50 can also obtain, from the blood pressure waveform time series data, blood pressure waveform data in the pre-exercise section corresponding to before the user exercises and blood pressure waveform data in the post-exercise section corresponding to after the user has exercised, and can then find an indicator expressing the effect of the exercise on the user's cardiac function on the basis of a speed (V) at which the characteristics of the blood pressure waveform, which have changed due to the exercise, return to the state found in the pre-exercise section.

As described thus far, using the biological information analyzing system 10 according to the present embodiment makes it possible to obtain a variety of information from the blood pressure waveform data. However, the biological information analyzing system 10 need not include functions for obtaining all of the above-described information. It is acceptable to provide only the functions for obtaining the necessary information, in accordance with the configuration, user, purpose of usage, location of usage, and so on of the biological information analyzing system 10. Additionally, the configuration may be such that the functions are provided as program modules (application software), and functions can be added by installing the required program modules in the biological information analyzing system 10.

The following Example describes a specific example of the application of the biological information analyzing system 10.

Example 1

This Example is an example in which the biological information analyzing system 10 is applied in the detection of pulse abnormalities.

Pulse abnormalities (irregular pulse waves or the like) may be signs of arrhythmia or signs of respiratory or cardiovascular abnormalities. Detecting the occurrence of pulse abnormalities at the appropriate timing is useful in reducing event occurrence risks.

Figure 7:
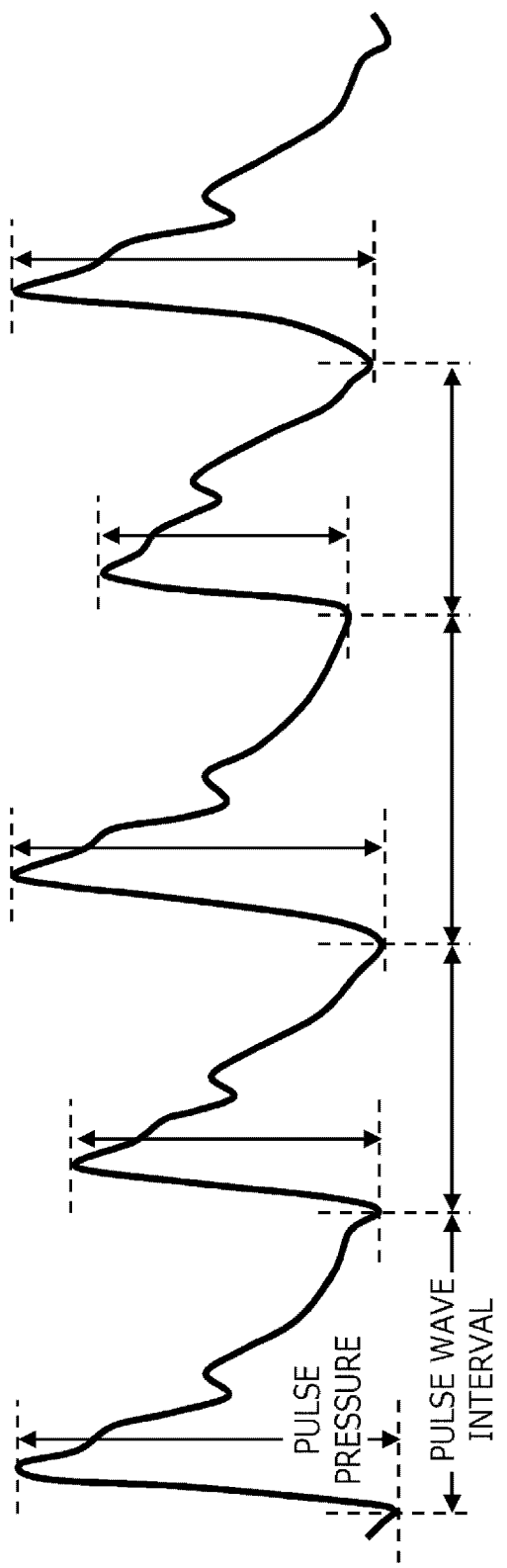
FIG. 7 is a diagram illustrating an example of a pulse abnormality according to Example 1.

Types of arrhythmia include extrasystoles, tachyarrhythmia, bradyarrhythmia, ventricular fibrillation, ventricular tachycardia, and so on. In all of these, the pulse wave is disturbed, and the effect of the disturbance appears as fluctuations/variations in the pulse wave interval (heartbeat period), pulse pressure, and so on (see FIG. 7). For example, with extrasystoles, unexpected contractions occur in the heart. Pulsations caused by unexpected contractions are weaker than normal, and since a clear blood pressure waveform is not formed, a phenomenon known as "missing pulse" occurs. In this case, the pulse wave interval will be 2-3 times the normal interval, and in some cases will be split among several groups of periods. With atrial fibrillation or the like, there are cases where pulse variations increase and the pulse period becomes random.

Figure 8:
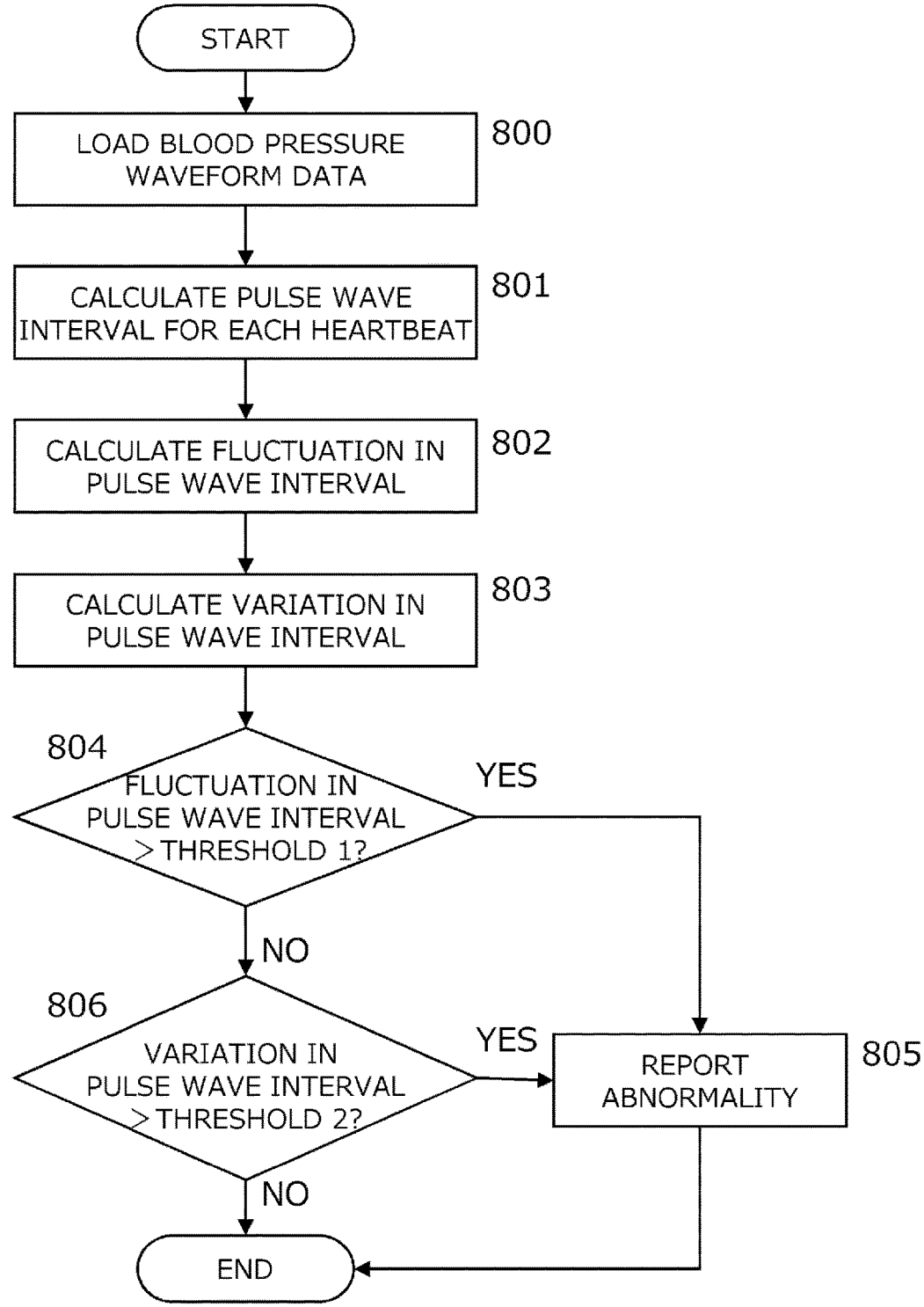
FIG. 8 is a flowchart illustrating a pulse abnormality detection process according to Example 1.

FIG. 8 illustrates an example of a flowchart of a pulse abnormality detection process according to this Example. First, the indicator extraction unit 50 loads the blood pressure waveform data from the storage unit 27 (step 800). For example, the most recent ten seconds' worth of time series data is loaded (if the sampling frequency is 100 Hz, this is 1000 points of blood pressure value data). The indicator extraction unit 50 carries out a characteristic point detection process on the blood pressure waveform data (see FIG. 6), and calculates the pulse wave interval of each heartbeat (step 801). The indicator extraction unit 50 then calculates the absolute value of the difference between the most recent pulse wave interval and a reference pulse wave interval (step 802). This value, i.e., the fluctuation in the pulse wave interval, is one indicator expressing the occurrence of a pulse abnormality. Note that the "reference pulse wave interval" is a standard value (normal value) for the pulse wave interval, and is, for example, the mean value of the pulse wave interval in normal blood pressure waveforms measured in the past. The reference pulse wave interval is stored in the storage unit 27 in advance, and the indicator extraction unit 50 loads the reference pulse wave interval from the storage unit 27 as necessary. Next, the indicator extraction unit 50 calculates variations (dispersion; standard deviation) in the pulse wave interval for a plurality of beats calculated in step 801 (step 803). The variations in the pulse wave interval are another indicator expressing the occurrence of a pulse abnormality.

Next, the processing unit 51 compares the fluctuation in the pulse wave interval calculated in step 802 with a threshold 1 (step 804), and if the fluctuation in the pulse wave interval exceeds the threshold 1, the processing unit 51 determines that the pulse wave interval is abnormal, and reports that abnormality through the output unit 25 (step 805). Additionally, the processing unit 51 compares the variation in the pulse wave interval calculated in step 803 with a threshold 2 (step 806), and if the variation in the pulse wave interval exceeds the threshold 2, the processing unit 51 determines that the pulse wave interval is abnormal, and reports that abnormality through the output unit 25 (step 805). Note that the threshold 1 and the threshold 2 are preferably stored in the storage unit 27 in advance, and are loaded from the storage unit 27 by the processing unit 51.

Figure 9:
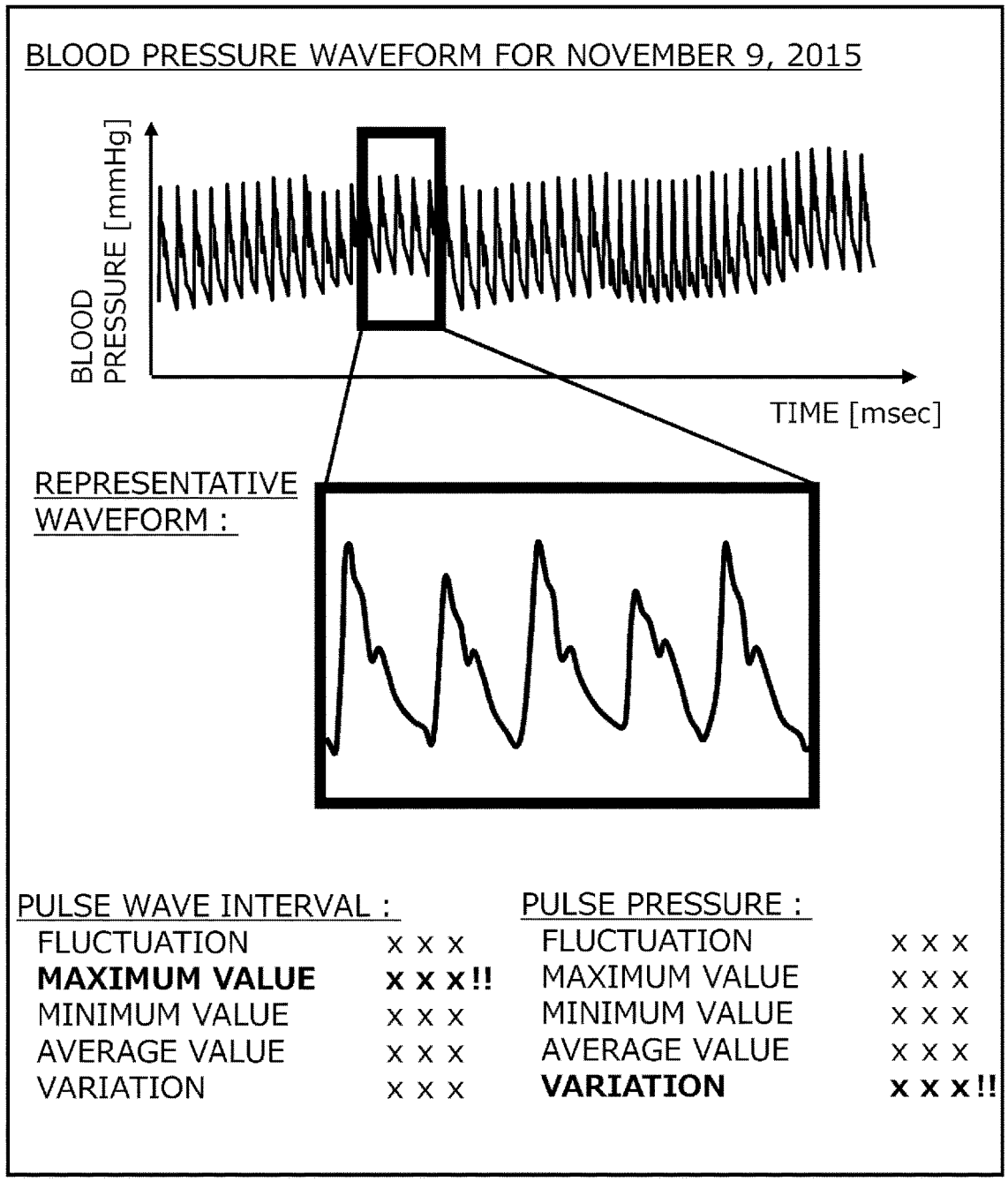
FIG. 9 is an example of an information output screen according to Example 1.

FIG. 9 is an example of an information output screen displayed in the output unit 25 by the processing unit 51. In the screen example illustrated in FIG. 9, a graph representing the blood pressure waveform time series data from Nov. 9, 2015, and an enlargement of a representative waveform extracted from that time series data, are displayed. Preferably, the processing unit 51 selects a waveform in a section confirmed as a pulse wave interval or pulse pressure fluctuation from the blood pressure waveform time series data as the representative waveform. The section extracted as the representative waveform is set to a length enabling the state of the pulse and the quality thereof to be confirmed (this length may be approximately several seconds to several tens of seconds, for example). The values of the indicators extracted by the indicator extraction unit 50 are displayed in the lower section of the screen. In the screen example illustrated in FIG. 9, fluctuations and statistical characteristics of the pulse wave interval (maximum value, minimum value, mean value, variation), and fluctuations in statistical characteristics of the pulse pressure (maximum value, minimum value, mean value, variation) are displayed. If the indicator values are values indicating the occurrence of a pulse abnormality, information indicating that the user's pulse is abnormal may be displayed. For example, a message such as "pulse wave interval maximum value exceeds reference value" or "pulse pressure varying greatly" may be output, or as in the example illustrated in FIG. 9, the indicators for which the abnormality has been determined may be emphasized, a sign such as an exclamation point may be added to the indicators for which the abnormality has been determined, or the like.

According to the configuration described above, the occurrence of pulse abnormalities can be detected quickly on the basis of the blood pressure waveform time series data, and reported to the user, a doctor, or the like. This makes it possible to quickly take appropriate responses as necessary before symptoms worsen.

Note that the configurations in the above-described embodiment and Example are merely specific examples of the present invention, and are not intended to limit the scope of the present invention. The present invention can employ a variety of specific configurations without departing from the technical spirit thereof. For example, although indicators are found using the pulse wave interval in the above-described Example, it is possible to detect abnormalities such as pulse variations by using pulse pressure (the difference between the systolic blood pressure and the diastolic blood pressure) instead of the pulse wave interval. Both the pulse wave interval and the pulse pressure may be used as well (e.g., a ratio between the pulse wave interval and the pulse pressure).

The technical spirit disclosed in the present specification can be specified as inventions such as those described below.

Addendum 1

A biological information analyzing device comprising:
a hardware processor; and
memory storing a program,
wherein through the program, the hardware processor:
extracts an indicator pertaining to a characteristic of a blood pressure waveform using data of the blood pressure waveform obtained by a sensor, which is worn on a user's body and can non-invasively measure a blood pressure waveform for each of heartbeats, continuously measuring the blood pressure waveform; and carries out a process based on the extracted indicator.

Addendum 2

A biological information analyzing system comprising:
a sensor, which is worn on a user's body and can non-invasively measure a blood pressure waveform for each of heartbeats;
a hardware processor; and
memory storing a program,
wherein through the program, the hardware processor:
extracts an indicator pertaining to a characteristic of the blood pressure waveform using data of the blood pressure waveform obtained by the sensor, which is worn on the user's body and can non-invasively measure the blood pressure waveform for each of heartbeats, continuously measuring the blood pressure waveform; and carries out a process based on the extracted indicator.

Addendum 3

A biological information analyzing method comprising:
a step of at least one hardware processor extracting an indicator pertaining to a characteristic of the blood pressure waveform using data of the blood pressure waveform obtained by the sensor, which is worn on the user's body and can non-invasively measure the blood pressure waveform for each of heartbeats, continuously measuring the blood pressure waveform; and
a step of at least one hardware processor carrying out a process based on the extracted indicator.

INDEX TO THE REFERENCE NUMERALS

1 . . . biological information analyzing device
2 . . . measurement unit
10 . . . biological information analyzing system
11 . . . main unit
12 . . . belt
20 . . . blood pressure measurement unit
21 . . . body movement measurement unit
22 . . . environment measurement unit
23 . . . control unit
24 . . . input unit
25 . . . output unit
26 . . . communication unit
27 . . . storage unit
30 . . . pressure sensor
31 . . . compression mechanism
300 . . . pressure detection element
50 . . . indicator extraction unit
51 . . . processing unit

The invention claimed is:

1. A biological information analyzing system comprising:
a compression mechanism comprising an air bladder and a fluid pump, the compression mechanism being configured to supply force against a body of a user;
a sensor adapted to be worn on the body of the user, the sensor being configured to non-invasively measure a blood pressure waveform for each heartbeat by continuously measuring the blood pressure waveform;
at least one processor configured to operate as:
an indicator extraction unit configured to extract an indicator pertaining to a characteristic of the blood pressure waveform using data of the blood pressure waveform obtained by the sensor; and
a processing unit configured to carry out a process based on the extracted indicator;
wherein the indicator extraction unit is configured to extract the indicator based upon a ratio between a pulse wave interval and a pulse pressure in the blood pressure waveform for a single heartbeat; and
wherein the processing unit is configured to output information indicating that a pulse of the user is abnormal when a value of the extracted indicator equals or exceeds a value indicating an occurrence of an abnormality, and
an output screen configured to display the output information, thereby notifying the user of the abnormal pulse,
wherein the sensor is configured to measure the blood pressure waveform in real time, and the processor is configured to extract the indicator and output the information in real time.

2. The biological information analyzing system according to claim 1, wherein the characteristic of the blood pressure waveform includes a characteristic of a shape of the blood pressure waveform for a single heartbeat.

3. The biological information analyzing system according to claim 1, wherein the characteristic of the blood pressure waveform includes a change in the blood pressure waveform over time.

4. The biological information analyzing system according to claim 1, wherein the characteristic of the blood pressure waveform includes a frequency component of the blood pressure waveform.

5. The biological information analyzing system according to claim 1, wherein the characteristic of the blood pressure waveform includes a statistical characteristic of the blood pressure waveform in a set section.

6. The biological information analyzing system according to claim 1, wherein the indicator extraction unit extracts an indicator pertaining to respiratory and/or circulatory function based upon at least one of: a characteristic of a shape of the blood pressure waveform for a single heartbeat, a change in the blood pressure waveform over time, a frequency component of the blood pressure waveform, and a statistical characteristic of the blood pressure waveform in a set section.

7. A non-transitory computer-readable medium storing a program causing a processor to function as the indicator extraction unit and the processing unit of the biological information analyzing system according to claim 1.

8. A biological information analyzing method comprising:
a step of supplying force against a body of a user;
a step of non-invasively measuring a blood pressure waveform of each heartbeat of the body of the user with a sensor adapted to be worn on the body of the user;
a step of extracting an indicator pertaining to a characteristic of the blood pressure waveform using data of the blood pressure waveform obtained by the sensor;
wherein extracting the indicator comprises extracting the indicator based upon a ratio between a pulse wave interval and a pulse pressure in the blood pressure waveform for a single heartbeat, and
a step of carrying out a process based on the extracted indicator;
a step of outputting information indicating that a pulse of the user is abnormal when a value of the extracted indicator equals or exceeds a value indicating an occurrence of an abnormality; and
a step of displaying the output information to the user, thereby notifying the user of the abnormal pulse
wherein the steps of measuring the blood pressure waveform, extracting the indicator, and outputting the information occur in real time.

* * * * *